United States Patent
Thomas

(10) Patent No.: US 6,796,966 B2
(45) Date of Patent: Sep. 28, 2004

(54) APPARATUS, AND KITS FOR PREVENTING OF ALLEVIATING VASOCONSTRICTION OR VASOSPASM IN A MAMMAL

(76) Inventor: Jeffrey E. Thomas, 6101 Imperata St., NE, Apt. #1616, Albuquerque, NM (US) 87111

( * ) Notice: Subject to any disclaimer, the term of this patent is extended or adjusted under 35 U.S.C. 154(b) by 0 days.

(21) Appl. No.: 10/068,551

(22) Filed: Feb. 5, 2002

(65) Prior Publication Data

US 2003/0026849 A1 Feb. 6, 2003

Related U.S. Application Data

(63) Continuation-in-part of application No. 09/165,561, filed on Oct. 2, 1998, now Pat. No. 6,358,536.
(60) Provisional application No. 60/062,419, filed on Oct. 15, 1997, and provisional application No. 60/069,824, filed on Dec. 16, 1997.

(51) Int. Cl.[7] .............................................. A61M 5/00
(52) U.S. Cl. ........................ 604/191; 604/82; 604/84; 604/87; 604/200; 604/218; 604/236; 222/386; 222/387
(58) Field of Search ......................... 604/187, 82–92, 604/181, 184, 186, 191, 199, 200, 207, 213, 218, 236, 244; 222/135, 386, 387, 388

(56) References Cited

U.S. PATENT DOCUMENTS

| | | | | |
|---|---|---|---|---|
| 3,557,787 A | * | 1/1971 | Cohen | 604/90 |
| 3,570,486 A | * | 3/1971 | Engelsher et al. | 604/88 |
| 3,678,931 A | * | 7/1972 | Cohen | 604/90 |
| 3,680,558 A | * | 8/1972 | Kapelowitz | 604/89 |
| 3,682,174 A | * | 8/1972 | Cohen | 604/90 |
| 3,749,084 A | * | 7/1973 | Cucchiara | 600/575 |
| 4,171,698 A | * | 10/1979 | Genese | 604/88 |
| 4,861,335 A | * | 8/1989 | Reynolds | 604/88 |
| 5,385,940 A | | 1/1995 | Moskowitz | |
| 5,429,603 A | * | 7/1995 | Morris | 604/88 |
| 5,496,284 A | * | 3/1996 | Waldenburg | 604/191 |
| 5,792,103 A | * | 8/1998 | Schwartz et al. | 604/82 |
| 5,820,583 A | * | 10/1998 | Demopulos et al. | 604/500 |

OTHER PUBLICATIONS

Joshi, S., Intraarterial Verapamil—but not Sodium Nitroprusside—Increases Cerebral Blood Flow in Patients with Arteriovenous Malformations, Journal of Neurosurgical Anesthesiology, Oct. 1996, 323, vol. 8, No. 4, Lippincott Williams & Wilkins.

Thomas, Jeffrey E. and McGinnis, Gerri, Safety of Intraventricular Sodium Nitroprusside and Thiosulfate for the Treatment of Cerebral Vasospasm in the Intensive Care Unit Setting, Stroke, Feb. 2002, 486–492, vol. 33(2), Lippincott Williams & Wilkins.

* cited by examiner

Primary Examiner—Michael J. Hayes
Assistant Examiner—Cris L. Rodriguez
(74) Attorney, Agent, or Firm—Benesch, Friedlander, Coplan & Aronoff LLP

(57) ABSTRACT

The invention relates to compositions, methods, apparatus, and kits for alleviating or preventing vasoconstriction or vasospasm in a mammal. The compositions, methods, apparatus, and kits are also useful for alleviating or preventing ischemic tissue damage resulting from ischemia associated with cerebral vasoconstriction which follows aneurysmal subarachnoid hemorrhage, with embolic stroke, with coronary artery obstruction, and with other conditions. These compositions, methods, apparatus, and kits generally relate to adventitial (i.e., extra-luminal) administration of a nitric oxide donor compound to a blood vessel in a mammal.

20 Claims, 10 Drawing Sheets

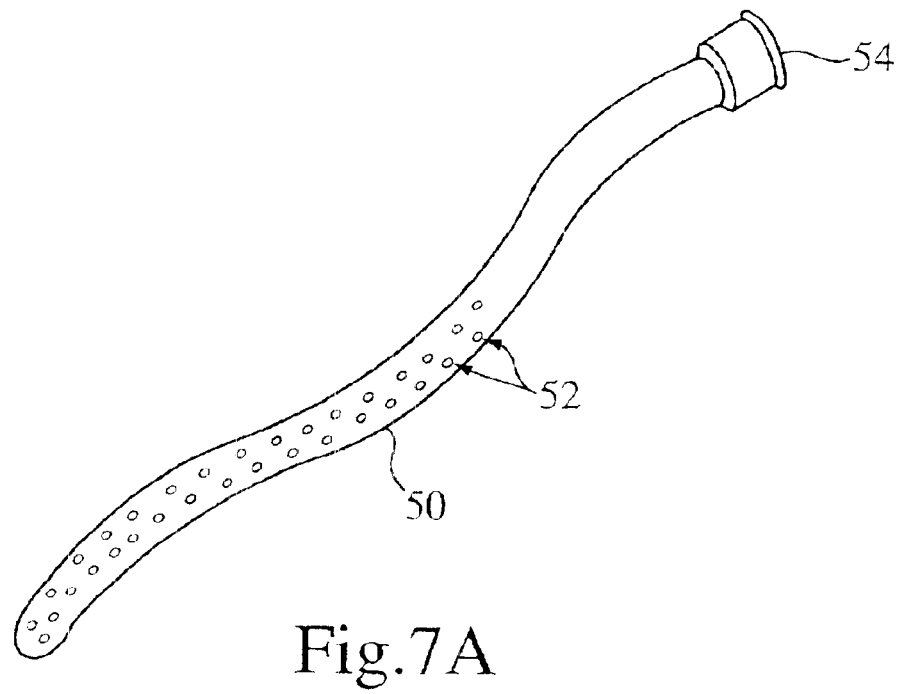
Fig.7A
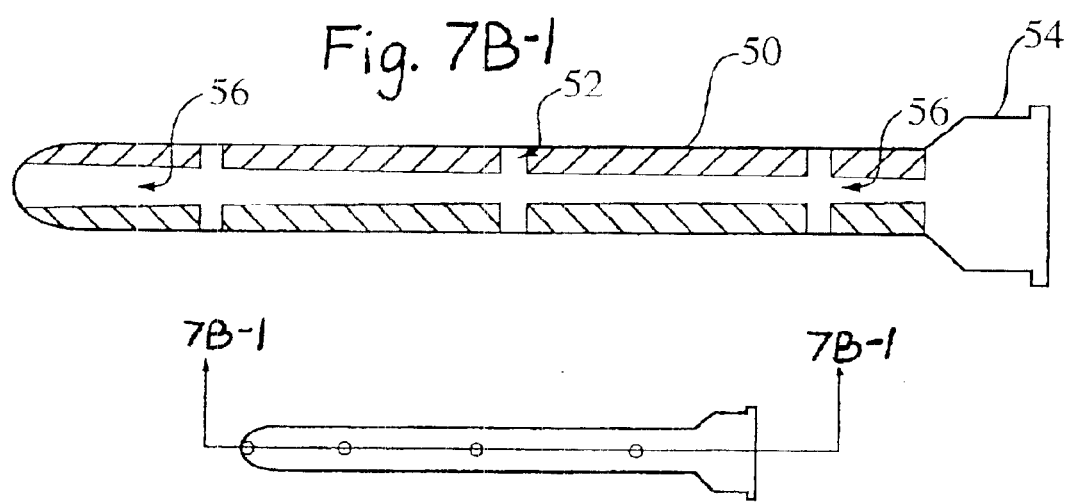
Fig. 7B-1
Fig. 7B-2

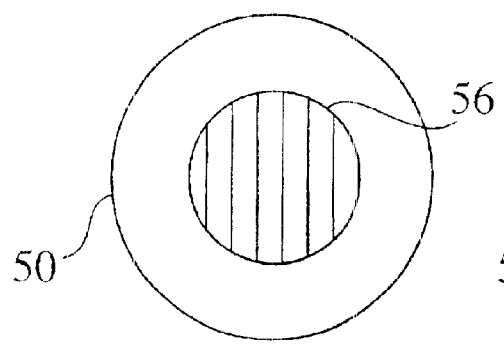
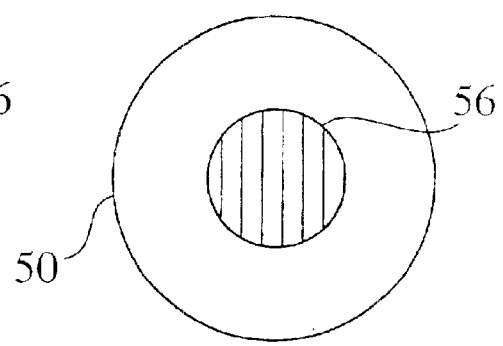
Fig.7C　　　　　Fig.7E
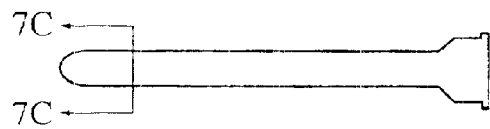
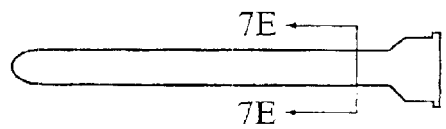
Fig. 7D　　　　　Fig. 7F
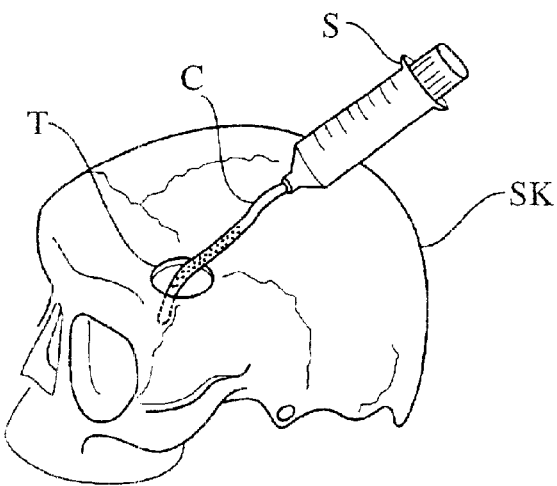
Fig. 7G

APPARATUS, AND KITS FOR PREVENTING OF ALLEVIATING VASOCONSTRICTION OR VASOSPASM IN A MAMMAL

CROSS REFERENCE TO RELATED APPLICATIONS

This application is a continuation-in-part of U.S. patent application Ser. No. 09/165,561 (now U.S. Pat. No. 6,358, 536) which was filed on Oct. 2, 1998 and is entitled to priority pursuant to 35 U.S.C. §119(e) to U.S. Provisional Patent Application No. 60/062,419, which was filed on Oct. 15, 1997, now abandoned and to U.S. Provisional Patent Application No. 60/069,824, which was filed on Dec. 16, 1997, now abandoned each of which is hereby incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

The field of the invention is alleviation of vasoconstriction and vasospasm. Vasoconstriction and vasospasm are important causes of ischemic damage in a wide variety of human maladies, including, for example, ischemic heart diseases such as myocardial infarction, angina pectoralis, and atherosclerotic injury, stroke, cerebral vasoconstriction, and cramps and ischemic muscle injury associated with muscle spasm.

Chronic delayed cerebral vasoconstriction (CDCV) following aneurysmal subarachnoid hemorrhage (SAH) is a serious and often fatal condition in humans. Considerable clinical and laboratory evidence has accumulated to indicate that endothelin-1 (ET-1) is involved in development of CDCV following SAH (Suzuki et al., 1990, Annals of Medicine 22:233–236; Suzuki et al., 1992, J. Neurosurgery 77:96–100; Fuwa et al., 1993, Neurologia Medico-Chirurgica 33:739–743; Kasuya et al., 1993, J. Neurosurgery 79:892–98; Ohlstein et al., 1992, J. Neurosurgery 77:274–278). A similar body of evidence exists for role of ET-1 in the failure of intrinsic vasodilatory mechanisms in the cerebral blood vessel wall as a result of SAH (Hongo et al., 1988, J. Neurosurgery 69:247–253; Snyder et al., 1992, Scientific American 266:68–77; Toda et al., 1993, Stroke 24:1584–1588).

The action of nitric oxide (NO) is implicated in intrinsic local vasodilation mechanisms. NO is the smallest biologically active molecule known and is the mediator of an extraordinary range of physiological processes (Nathan, 1994, Cell 78:915–918; Thomas, 1997, Neurosurg. Focus 3:Article 3). NO is also a known physiologic antagonist of endothelin-1, which is the most potent known mammalian vasoconstrictor, having at least ten times the vasoconstrictor potency of angiotensin II, which has been implicated in CDCV by many investigations (Yanagisawa et al., 1988, Nature 332:411–415; Kasuya et al., 1993, J. Neurosurg. 79:892–898; Kobayashi et al., 1991, Neurosurgery 28:5:673–679). The biological half life of NO is extremely short (Morris et al., 1994, Am. J. Physiol. 266:E829–E839; Nathan, 1994, Cell 78: 915–918, 1994). NO accounts entirely for the biological effects of endothelium-derived relaxing factor (EDRF) and is an extremely potent vasodilator that works through the action of cGMP-dependent protein kinases to effect vasodilation (Henry et al., 1993, FASEB J. 7:1124–1134; Nathan, 1992, FASEB J. 6:3051–3064; Palmer et al., 1987, Nature 327:524–526; Snyder et al., 1992, Scientific American 266:68–77).

As a free radical gas, NO is difficult to measure directly, but two pieces of evidence support its insufficiency or dysfunction during SAH-induced cerebral vasospasm. First, cGMP is depleted in the vessel wall following SAH and second, oxyhemoglobin, released by erythrocyte lysis in the SAH clot, binds NO avidly (Gibson et al., 1957, Am. J. Physiol. 136:507–526; Kim et al., 1992, Circulation Research 70:248–56; Martin et al., 1985, J. Pharmacol. Exp. Ther. 232:708–716).

It is likely that the phenomenon of CDCV simultaneously involves the increased activity of ET-1 and the decreased activity of NO. Validation of such a hypothesis requires that attenuation or reversal of CDCV by either interfering with the action of ET-1 or by somehow making NO more available to the blood vessel wall is demonstrated. This has been attempted by several groups of investigators using different methods with varying degrees of success. The former strategy has enjoyed more popularity in the recent literature and the use of endothelin receptor antagonists to attenuate CDCV has provided promising initial results (Foley et al., 1994, Neurosurgery 34:108–113; Itoh et al., 1994, J. Neurosurgery 81:759–764).

One important limitation of the use of NO donors in vivo has been their tendency to induce severe systemic hypotension (Heros et al., 1976, Surgical Neurology 5:354–362; Raynor et al., 1963, J. Neurosurgery 20:94–96). A reliably effective treatment for CDCV that follows aneurysmal SAH remains elusive. The mainstay of treatment for this complication, now the most important cause of mortality and neurological morbidity following aneurysmal SAH, is hypertensive/hypervolemic/hemodilution (HHH) therapy (Solomon et al., 1998, Neurosurgery 23:699–704). Because severe cases of CDCV are refractory to HHH therapy, and because some patients do not tolerate HHH therapy for medical reasons, an alternative treatment for CDCV is needed. Effective treatments for vasoconstriction and vasospasm in cerebral and other tissues are needed, as are prophylactic treatments for preventing vasoconstriction and vasospasm.

The present invention satisfies these needs.

BRIEF SUMMARY OF THE INVENTION

The invention relates to a method of alleviating vasoconstriction in a mammal. The method comprises adventitially administering a nitric oxide donor compound to a constricted blood vessel in the mammal. Constriction of the blood vessel is thereby alleviated. In one embodiment of this method, the animal is a human. The blood vessel can, for example, be one that supplies blood a tissue selected from the group consisting of an erectile tissue (e.g., penile or clitoral tissue), an ocular tissue, a non-cardiac muscle tissue (e.g., a spastic muscle tissue), a non-cerebral neuronal tissue (e.g., a peripheral afferent or efferent nerve, retina, or an optic nerve of a patient afflicted with diabetic retinopathy), and an epithelial or endothelial tissue such as a skin tissue or an oral tissue. The compound can be administered directly to the tissue (e.g., by topically applying it to a normally or surgically exposed tissue or by injecting it into the tissue) or it can be administered to a fluid that normally contacts the tissue. By way of example, a solution of a nitroprusside salt or adenosine can be administered to an ocular tissue by applying the solution directly to the eyeball, by providing the solution to lacrimal fluid surrounding the eyeball, or by injecting the solution into an ocular compartment containing the aqueous or vitreous humor of the eye.

In one embodiment of this method, the compound is administered in the form of a sustained-release formulation of the compound. The compound can, for example, be selected from the group consisting of nitroglycerine, arginine, and a nitroprusside salt. Preferably, the compound is sodium nitroprusside (SNP). The dosage of SNP for established vasospasm in an adult human in a one-day period is in the range from about 10 milligrams to 88 milligrams, more preferably from about 10 milligrams to 30 milligrams. Prophylactic treatment can comprise administration of a composition comprising an amount of a NO donor compound in the range from less than 1 milligram to about 10 milligrams, preferably in the range of from about 2 milligrams to 4 milligrams, the composition being administered 1 to about 5 times per day, and preferably 1 to 3 times per day. The amount of the compound administered daily for prophylactic purposes should not exceed about 24 milligrams. The NO donor compound can be administered in conjunction with or, in certain situations, replaced with a vasodilating compound that is not an NO donor compound. By way of example, adenosine is known to be a potent vasodilator. Inhibition, prevention, or reversal of vasoconstriction and vasospasm effected by one or both of an NO donor compound or a vasodilating compound can reduce or prevent ischemic tissue damage that would occur if the vasoconstriction or vasospasm were left untreated. Thus, in one embodiment, the NO donor compound, the non-NO-donor vasodilating compound, or both are chronically administered to a blood vessel that supplies the tissue (e.g., a blood vessel situated within the tissue) in order to inhibit or prevent ischemic damage in the tissue. By way of example, an NO donor compound, a vasodilating compound, or both can be chronically (e.g., repeatedly or continuously over a period of days, weeks, months, or years) administered to the cerebrospinal fluid of a human patient so that the compound(s) contact the adventitial surface of cerebral blood vessels and inhibit or prevent constriction or spasm of those vessels. Inhibition or prevention of cerebral vasoconstriction and vasospasm can reduce or eliminate ischemic damage to cerebral tissue. Reduction or elimination of this damage can inhibit, prevent, or reduce the severity of, cerebral ischemic disorders such as stroke, altitude-related mental confusion, and chronic dementia.

In another embodiment of this method, the NO donor compound is administered in the form of a pharmaceutical composition comprising the compound and a scavenger compound selected from the group consisting of a cyanide scavenger, a cyanate scavenger, hydroxycobalamin, and thiosulfate.

Preferably, the amount of the NO donor compound administered to the blood vessel is an amount that is sufficient to alleviate constriction of the blood vessel, but that is insufficient to induce systemic hypotension or cerebral hypertension in the mammal.

Another embodiment of this method comprises administering to the mammal a compound selected from the group consisting of an anti-inflammatory agent, an antibiotic, an oxyhemoglobin-reducing compound, a thrombolytic agent, and an anti-emetic compound to the mammal.

The invention also relates to a method of inhibiting or preventing vasoconstriction in a mammal. This method comprises adventitially administering a nitric oxide donor compound to a blood vessel in the mammal, whereby constriction of the blood vessel is prevented. Preferably, the nitric oxide donor compound is sodium nitroprusside. Also preferably, the mammal is a human, and the amount of sodium nitroprusside administered to the human in a one-day period is not more than 24 milligrams, more preferably in the range from 4 to 24 milligrams. Also preferably, the nitric oxide donor compound is administered in the form of a pharmaceutical composition comprising a sustained-release formulation of the compound. Vasoconstriction can also be inhibited or prevented by adventitial administration of a vasodilator such as adenosine to the blood vessel.

The invention further relates to a method of dilating a constricted or spastic blood vessel in a mammal. This method comprises adventitially administering a nitric oxide donor compound or another type of vasodilating compound (e.g., adenosine, hydralazine, or minoxidil) to the blood vessel, whereby the blood vessel dilates.

The invention further relates to a method of alleviating ischemia in a tissue of a mammal. This method comprises administering a nitric oxide donor compound to the tissue, whereby a blood vessel in the tissue is exposed to the compound, thereby alleviating constriction or spasm of the blood vessel and alleviating ischemia in the tissue.

The invention still further relates to a method of inhibiting or preventing ischemia in a tissue of a mammal. This method comprises administering a nitric oxide donor compound to the tissue, whereby the compound is administered to a blood vessel in the tissue, thereby inhibiting or preventing constriction of the vessel and inhibiting or preventing ischemia in the tissue. Constriction of the blood vessel and ischemia in a tissue to which blood supply is provided by the vessel can also be inhibited or prevented by adventitially administering a vasodilating compound other than an NO donor compound to the vessel. By way of example, adenosine or another known vasodilator can be adventitially administered to the vessel to inhibit or prevent ischemic damage to a tissue supplied by the vessel.

The invention also relates to a vasodilating composition for adventitial administration to a constricted or spastic blood vessel of a mammal, the composition comprising a nitric oxide donor compound and a pharmaceutically acceptable carrier. Preferably, the pharmaceutically acceptable carrier is selected from the group consisting of the cerebrospinal fluid of the mammal and a synthetic cerebrospinal fluid.

In addition, the invention further relates to a device for delivering to a mammal a pharmacological agent having a short half-life in solution. This device comprises:

a first hollow body having a flow orifice, a first fluid access port, and a first pressure orifice, each in fluid communication with the interior of the first hollow body;

a second hollow body for containing the pharmacological agent, the second body having a second fluid access port in fluid communication with the interior of the second hollow body and in fluid communication with the first fluid access port, and an outlet port in fluid communication with the interior of the second hollow body; and a first pressure modulator connected to the first pressure orifice.

In one embodiment, this device further comprises a valve having an inlet orifice coupled to the outlet port and an outlet orifice, wherein the valve permits fluid flow in the direction from the inlet orifice to the outlet orifice. Preferably, the outlet orifice is in fluid communication with the interior of the first hollow body In another embodiment of this device, the second hollow body contains the pharmacological agent in the interior thereof. Preferably, the pharmacological agent is a nitric oxide donor compound, even more preferably a single human intrathecal delivery amount of the nitric oxide donor compound.

In yet another embodiment of this device, the second hollow body further comprises at least one compartment containing the pharmacological agent, wherein the interior of the compartment is separated from the interior of the second hollow body by a breachable barrier. Preferably, the breachable barrier comprises a polymeric film or a foil, such as a film having at least one score or a film having at least one perforation. In one version, this device further comprises a compartmental plunger slidably disposed within the compartment for breaching the barrier, wherein when the compartmental plunger is actuated, the barrier is breached, whereby the composition is brought into fluid communication with the interior of the second hollow body.

In another embodiment of device of the invention, the pressure modulator comprises a first plunger snugly slidably disposed within the interior of the first hollow body, the first plunger being positionable within the first hollow body between an advanced position and a retracted position, wherein the flow orifice is not in fluid communication with the fluid access port when the first plunger is positioned in the advanced position, and wherein the flow orifice is in fluid communication with the fluid access port when the first plunger is positioned in the retracted position. Preferably, the device of this embodiment further comprises a second plunger snugly slidably disposed within the second hollow body, whereby when the second plunger is urged in the direction of the outlet port, the contents of the second hollow body are discharged through the outlet port. Thus, according to one embodiment, the first hollow body is a first syringe, wherein the second hollow body is a second syringe, and the interiors of the first and second syringes are connected to the interior of a ventriculostomy or other subarachnoid space-accessing device (e.g., any of a variety of catheters) by means of a three-way valve, wherein the three-way valve selectably connects any two of the interior of the first syringe, the interior of the second syringe, and the interior of the ventriculostomy.

In another embodiment of the device of the invention, the second hollow body is disposed within the interior of the first hollow body; the first hollow body and second hollow body are substantially longitudinally coaxial; the outlet orifice is disposed in close proximity to the flow orifice; and the flow orifice is adaptable to a cerebrospinal fluid drainage system.

The invention also relates to a subdural catheter comprising a flexible, generally tubular body having an outer surface, a proximal end, a distal end, a lumen extending within the body from the proximal end, at least one hole extending through the body from the outer surface to the lumen, and a hub at the proximal end for attaching the catheter to a fluid handling device. Preferably, the body has a flattened cylindrical shape. Also preferably, the body is at least partially radio opaque. In one embodiment of the subdural catheter, the width of the lumen at the distal end of the body is greater than the width of the lumen at the proximal end of the body.

The invention further relates to a subdural insertional guide. The guide comprises a substantially rigid body having a long axis, a proximal end, a distal end, an outer surface, and a lumen extending within the body from the proximal end to the outer surface, wherein the lumen extends generally parallel to the long axis at the proximal end of the body and generally perpendicular to the long axis at the outer surface, wherein when the distal end of the body is inserted into a trephination in the skull of a mammal, the lumen is in fluid communication with a subdural space in the mammal. In one embodiment, the subdural insertional guide further comprising an inflatable balloon at the distal end of the body.

The invention still further relates to a kit for dilating a blood vessel in a mammal. This kit comprises a nitric oxide donor compound (or another vasodilating compound such as adenosine) and an instructional material which describes adventitially administering the compound to a blood vessel of the mammal.

The invention yet further relates to a kit for dilating a constricted or spastic blood vessel in a mammal. This kit comprises at least one syringe containing a nitric oxide donor compound in a substantially anhydrous form and a three-way valve for connecting the syringe with a second syringe and with a liquid conduit in fluid communication with the adventitial surface of a the blood vessel.

The invention also relates to a kit for intrathecal administration of a nitric oxide donor compound to a mammal. This kit comprises:

a) a device for administering the compound, the device comprising:

a first hollow body having a flow orifice, a first fluid access port, and a first pressure orifice, each in fluid communication with the interior of the first hollow body;

a second hollow body for containing the compound, the second body having a second fluid access port in fluid communication with the interior of the second hollow body and in fluid communication with the first fluid access port, and an outlet port in fluid communication with the interior of the second hollow body; and a valve having an inlet orifice coupled to the outlet port and an outlet orifice, wherein the valve permits fluid flow in the direction from the inlet orifice to the outlet orifice; and b) an instructional material which describes use of the device to intrathecally administer the compound to the mammal.

The invention further relates to a subdural catheterization kit comprising a subdural catheter comprising a flexible, generally tubular catheter body having an outer surface, a proximal end, a distal end, a lumen extending within the catheter body from the proximal end, at least one hole extending through the catheter body from the outer surface to the lumen, and a hub at the proximal end for attaching the catheter to a fluid handling device; and, a subdural insertional guide, the guide comprising a substantially rigid guide body having a long axis, a proximal end, a distal end, an outer surface, and a lumen extending within the guide body from the proximal end to the outer surface, wherein the lumen extends generally parallel to the long axis at the proximal end of the guide body and generally perpendicular to the long axis at the outer surface, wherein when the distal end of the guide body is inserted into a trephination in the skull of a mammal, the lumen is in fluid communication with a subdural space in the mammal.

BRIEF DESCRIPTION OF THE SEVERAL VIEWS OF THE DRAWINGS

FIG. 1, comprising FIG. 1B is a reproduction of a video image of basilar artery illustrating a severely constricted artery.

FIG. 2, comprising FIG. 2B is a reproduction of a video image illustrating no sign of constriction after 30 minutes in the same artery shown in FIG. 1B.

FIG. 6, comprising FIG. 6A is a frontal cross-sectional view of the apparatus, and FIG. 6B is an axial cross-sectional view. FIGS. 6C–6E depict an optional embodiment of the apparatus. FIG. 6C is a frontal cross-sectional view of the optional embodiment, FIG. 6D is an axial cross-sectional view, and FIG. 6E is a detail of the operation of the optional embodiment.

FIG. 7, comprising FIGS. 7A, 7B-1, 7B-2, 7C, 7D, 7E, 7F, and 7G, is a diagram of a subdural catheter. FIGS. 7B-1 and 7B-2 depict a cross-sectional view of the catheter. FIGS. 7C and 7D depict another cross-sectional view of the catheter. FIGS. 7E and 7F depict yet another cross-sectional view of the catheter. FIG. 7G depicts operation of the catheter.

FIG. 8, comprising FIGS. 8A and 8B are frontal views of embodiments of the guide. FIG. 8C is a detail of the guide. FIG. 8D depicts operation of the guide and the catheter depicted in FIG. 7.

DETAILED DESCRIPTION OF THE INVENTION

Figure 1A:
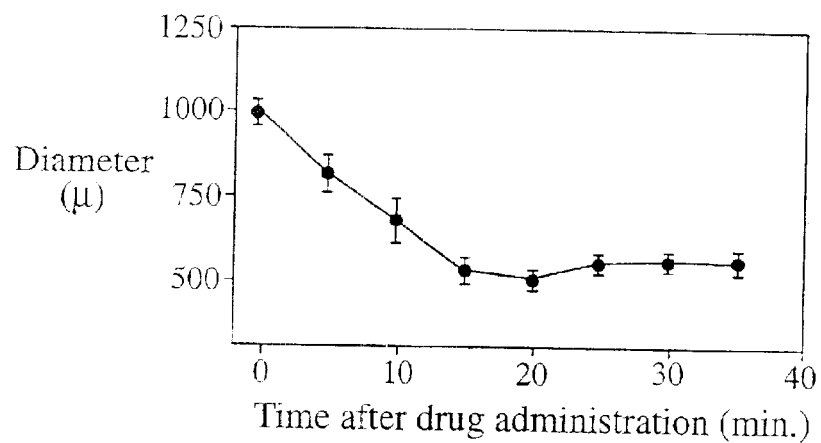
FIGS. 1A and 1B, is graph (FIG. 1A) and an image (FIG. 1B) depicting the effect of ET-1 on the basilar artery of the rabbit after subarachnoid administration.

The invention relates to methods of alleviating and preventing vasoconstriction and vasospasm in mammals, in both veins and arteries. It has been known that systemic delivery of NO or NO donor compounds induces severe and dangerous systemic hypotension. For this reason, NO donor compounds have not been used to treat vasospasm and vasoconstriction. Similarly, other vasodilating agents can exert their effects throughout the body if they are administered systemically. As described herein, it has been discovered that adventitial administration (i.e., administration to the non-luminal surface) of NO donor compounds to blood vessels alleviates or reverses vasoconstriction or vasospasm in the blood vessel. Adventitial administration of other vasodilating compounds (e.g., adenosine) can also be used to inhibit, prevent, or alleviate vasoconstriction and vasospasm.

It has also been discovered that delivery of one or more NO donor compounds (or another vasodilating compound) to a body fluid which contacts a blood vessel alleviates vasoconstriction or vasodilation in the blood vessel. This discovery is particularly useful for relieving vasoconstriction and vasospasm in blood vessels which, because of their body location, cannot be easily treated directly. For example, some blood vessels which supply cardiac and cerebral tissues are located relatively deep within the body, and are surrounded by bony and other tissues which can be difficult to surgically manipulate without causing severe trauma to the subject. Beneficially, the present invention permits a NO donor compound or other vasodilator to be delivered to a body cavity (e.g., the pericardial cavity for coronary arteries, and the subarachnoid cavity for cerebral arteries) and to be therein transported to the adventitial surface of blood vessels located within that cavity, thereby relieving vasoconstriction or vasospasm of the blood vessels, or dilating the vessels. In one embodiment, a nucleic acid vector (e.g., DNA or RNA in a viral or non-viral expression vector) encoding an enzyme (e.g., arginase or NO synthase) that catalyzes production of NO is provided to the cavity or directly to a tissue in the patient's body. Expression of the nucleic acid vector in the patient's cells induces NO formation at the site for a period of hours, days, weeks, months, or even years, thereby providing prolonged effect.

Dilation of blood vessels, such as that effected by alleviating or reversing vasoconstriction and vasospasm enables enhanced blood flow through the vessel, thereby improving oxygen supply to the tissues supplied by the vessel and vessels proximal and distal thereto. Thus, the compositions and methods of the invention are useful not only for relieving vasoconstriction and reversing vasospasm, but also for alleviating ischemia associated with these conditions.

The invention includes a method of alleviating any type of vasoconstriction or vasospasm in a mammal, preferably a human. This method comprises adventitially administering at least one NO donor compound to a constricted or spastic blood vessel in the mammal. In a preferred embodiment, the method involves treatment of early embolic stroke in a human. In another preferred embodiment, the method involves treatment of CDCV following aneurysmal SAH in a human. Thus, at least in one aspect of the invention, the method comprises intrathecally administering an NO donor compound to a human. In other aspects, the invention relates to treatment (i.e., alleviation, inhibition, prevention, or reversal) of disorders associated with disturbance or obstruction of peripheral blood circulation, such as in diabetic microangiopathy. Enhanced peripheral blood flow can be achieved by adventitially administering an NO donor compound or other vasodilator to one or more blood vessels (i.e., major, named vessels, microvasculature that varies individually in patients, or both) in the region or tissue in which abnormal peripheral blood circulation occurs to thereby treat the disorder. Disorders in which enhancement of peripheral blood circulation is desirable include erectile dysfunction, sexual dysfunction in both males and females, wound healing, diabetic retinopathy, and oral disorders such as periodontal disease, oral surgery wounds, and microbial infections. Disturbed or obstructed peripheral blood circulation can affect the rate at which wounds heal, including wounds resulting from oral surgery (e.g., surgical repairs, grafts, or incisions within the mouth).

Inhibiting, preventing, or alleviating vasoconstriction, vasospasm, or both, can improve blood supply to a tissue (i.e., improve delivery of oxygenated blood to or removal of de-oxygenated blood from the tissue). Improved blood supply can inhibit, prevent, or alleviate occurrence of an ischemic disorder in the tissue or of another disorder mediated by aberrant blood supply to the tissue (e.g., an erectile disorder). The methods described herein are especially useful for inhibition, prevention, and alleviation of disorders that affect tissues that have relatively sparse blood supply (e.g., cartilage tissue, ocular tissues, and certain peripheral nervous tissues, such as the retina and various peripheral nerves) or tissues in which the functionality of the tissue is heavily dependent on sufficiency of the blood supply (e.g., erectile tissues such as penile and clitoral tissues).

Blood supply to wounded tissue is often disrupted owing to trauma, inflammatory responses, and tissue necrosis. Adventitial administration of an NO donor compound or another vasodilator to wounded tissue (e.g., by topical administration to the wound) can improve blood supply to the wounded tissue, enhancing the speed, extent, and quality of wound healing that is achieved.

In an important embodiment, the invention relates to the treatment of cerebral vasoconstriction in a human patient by intrathecally administering to the patient one or more NO donors. Several embodiments of a device useful for intrathecal delivery of one or more NO donors to a human or other mammalian patient are described herein, as are methods of their use. According to this embodiment of the present invention, intrathecal administration of an NO donor to a mammal, preferably, a human, results in alleviation of vasoconstriction without concomitant systemic hypotension or intracranial hypertension. As the data presented herein establish, intrathecal administration of an NO donor serves to counteract the effects of ET-1 induced vasospasm following aneurysmal SAH.

Intrathecal administration of one or more NO donor compounds to alleviate or prevent cerebral vasoconstriction or vasospasm is also useful for alleviating, minimizing, or preventing ischemic brain damage associated with embolic stroke in a mammal (e.g., a human). Intrathecal administration of an NO donor to a mammal which is presently experiencing, or which has recently (i.e., within minutes, hours, or even days) experienced an embolic or other type of stroke (or other type of cerebral ischemia) alleviates and prevents cerebral vasoconstriction and vasospasm in the mammal, thereby minimizing, alleviating, or preventing ischemic tissue damage which results from the impaired oxygen supply associated with cerebral vasoconstriction and vasospasm.

The invention also relates to a method of treatment, wherein the treatment is prophylactic rather than therapeutic, that is, the method is useful for the prevention of vasoconstriction or vasospasm in a situation in which vasoconstriction or vasospasm is anticipated, either imminently or during a period during which a sustained-release formulation of an NO donor compound persists in a mammal such as a human. This method involves the administration of an amount of an NO donor to a blood vessel, such as a blood vessel which is or is anticipated to become constricted, in a mammal such as a human. In this aspect of the method of the invention, the NO donor is delivered to the adventitial or abluminal side of the blood vessel in order to achieve the prophylactic effect. Prophylactic anti-vasoconstrictive or anti-vasospastic treatment is indicated in individuals who, for any of a wide variety of medical reasons, are considered to be "at risk" for vasoconstriction or vasospasm. Specifically, there are medical circumstances wherein vasoconstriction is either anticipated after a delay, as in cerebral vasospasm that follows SAH, or is observed during an earlier phase of its progression. In the latter instance, this may occur in vasoconstriction that is identified during a medical or surgical procedure and is expected to progress, either independently as a part of its natural history, or as a result of manipulation in the medical setting. Such circumstances are particularly common during surgical procedures, e.g., vasoconstriction that is caused by mechanical manipulation of blood vessels. Examples of such surgery include brain surgery, spinal surgery, extracranial, vascular and cardiac surgery, endovascular surgical manipulation using catheters, or any surgical procedure wherein blood vessels are manipulated intentionally or otherwise. The beneficial effects of the invention applied in this manner have been observed and documented by the inventor. It is conceivable that ischemia of the heart, brain or other organs or tissues can thus be prevented, minimized, or arrested by the timely administration of an NO donor according to the methods of the invention. Thus, administration of an NO donor to the outer or abluminal part of the blood vessel, under widely varying circumstances such as thromboembolism, stroke, heart attack, blood dyscrasias or vasculitis is contemplated as part of the present invention.

An NO donor compound or another vasodilating compound can be administered to substantially any tissue in, on, through, or in fluid communication with which a blood vessel passes, so long as the compound is able to migrate through, past, or around the tissue to reach the adventitial (abluminal) side of the vessel. Examples of tissues to which one or more of these compounds can be administered in order to inhibit, prevent, or alleviate vasoconstriction or vasospasm include muscle tissues (including skeletal, smooth, and cardiac muscle tissues), neuronal tissues (e.g., cerebral and cephalic tissues, spinal cord, and efferent and afferent peripheral nerves), ocular tissues (e.g., eye and eye socket tissues), erectile tissues (e.g., penile and clitoral tissues), and epithelial and endothelial tissues (e.g., skin, mucus membranes of the gastrointestinal and pulmonary tracts, and exterior and interior linings of organs). One or more of the compounds can also, or instead, be administered to a fluid that contacts one of these tissues, such as cerebrospinal fluid (which contacts cerebral tissue and cerebral blood vessels) and lacrimal fluid (which contacts several ocular tissues).

The NO donor compound can be substantially any compound which, under physiological conditions in the tissue of the mammal to which the compound is to be administered, decomposes or otherwise reacts to generate NO. Physiological conditions in numerous mammalian tissues under a wide variety of circumstances are known, and the physiological conditions in previously non-characterized tissues or instances can be readily be determined by the skilled artisan using well known techniques.

Examples of NO donor compounds which are contemplated for use in the compositions, methods, apparatus, and kits of the invention include one or more of nitroglycerine (NTG), a nitroprusside salt such as sodium nitroprusside (SNP), arginine, or any other NO-generating compound. Compounds which are not known to be NO donor compounds at the time the present disclosure was prepared can nonetheless be used as soon as their NO-generating properties are known, since the chemical identity of the NO donor compound of the invention is not critical. Where more than one NO donor compound is administered to a subject, the multiple compounds can, for example, be administered either in admixture, separately but simultaneously, or sequentially. An NO donor compound can be modified so as to constitute a formulation comprising multiple molecules of nitric oxide per single molecule of the carrier compound, e.g., a branched-molecule preparation.

When only a single NO donor compound is administered to a mammal, SNP is the preferred NO donor compound. A combination of, for instance, NTG and SNP can be administered to a mammal in instances where the effect(s) of administering SNP alone are adverse to the host. If that is the case, NTG can be administered along with SNP in order to provide the mammal with the required amount of NO without the attendant side effects of SNP administration. When both of NTG and SNP are used sequentially in a human, SNP is preferably used first.

NO can be administered to a mammal in the form of a composition comprising L-arginine and an agonist of the enzyme, NO synthase, as described in U.S. Pat. No. 5,543, 430. Alternately, L-arginine and NO synthase can be administered together to an adventitial blood vessel site. NO synthase occurs in many distinct isoforms, including a constitutive form that is present in normal endothelial cells, neurons, and some other tissues. The inducible form of NO synthase is present in activated macrophages and is also induced in vascular smooth muscle cells. Administration of L-arginine and an agonist of NO synthase serves to promote in vivo generation of NO, thereby effectively administering NO to the mammal. In vivo generation of NO can also be promoted by delivering a nucleic acid vector to a cell of the mammal, where the vector encodes an enzyme that catalyzes formation of NO under physiological conditions or upon addition of a non-physiological substrate.

Inhibition, prevention, or alleviation of cerebral vasoconstriction, cerebral vasospasm, or both, can be achieved by adventitially administering a vasodilating compound other than an NO donor compound to one or more cerebral blood vessels, such as those listed herein. By way of example, adenosine or another non-NO-donor vasodilating compound can be administered to cerebrospinal fluid or placed within the subdural or (preferably) intrathecal space in a relatively slowly-released form in order to provide the vasodilating compound to the adventitial surface of a cerebral blood vessel over a prolonged period of hours, days, weeks, or months. Examples of such compositions have been described (Tierney et al., 2001, Neurosurgery 49:945–951; Thai et al., 1999, Stroke 30:140–147).

The blood vessel can be in any part of the body where access to the blood vessel can be made by indirect (e.g., via catheter or endoscope) or direct surgical means. By way of example, during cardiac surgery, dilation of constricted coronary vessels may be desired to enhance blood flow or improve the technical maneuvers of the surgery itself. Also by way of example, pericardial administration of an NO donor may be desired under circumstances of acute myocardial ischemia, via needle or catheter, in a manner similar to the situation wherein acute brain ischemia can be treated by adventitial delivery of the NO donor as described herein. Delivery of a therapeutic compound to the adventitial surface of a blood vessel, or to a body fluid or body cavity which is fluid communication with that surface, is well known in the art, and can be achieved by any of numerous routes, such as via needle, catheter, or by direct surgery.

To administer an NO donor compound or another vasodilating compound adventitially to a blood vessel of a mammal, the compound is provided, alone, in solution, in suspension, in a pharmaceutical composition, or in a sustained-release pharmaceutical composition, to a body fluid or to a body cavity which is in fluid communication with the exterior (i.e., adventitial or abluminal) surface of the blood vessel or directly to the exterior surface of the blood vessel. Because NO is a very small compound which is capable of diffusing through tissue to a limited degree, the compound can also be provided to a fluid, cavity, or tissue which is in fluid communication with a thin layer (i.e., no more than ten cell layers and preferably fewer, such as one or two cell layers) of tissue which covers the adventitial surface of the blood vessel. Thus, for example, an NO donor compound can be delivered adventitially to a blood vessel near the surface of the skin by topically applying a composition comprising the NO donor compound to the surface of the skin. Similarly, other vasodilating compounds can act at the outer surface of a blood vessel or, depending on their solubility in vascular tissues and the thickness and permeability of the vascular tissue, can diffuse through the vascular wall to act at locations nearer the lumenal surface of the vessel. By way of example, adenosine can activate receptors present on the surface of cells of the adventitial face of a blood vessel or it can penetrate into the vascular tissue and activate receptors present throughout the vascular tissue.

In a preferred embodiment of the invention, a composition comprising an NO donor compound is administered adventitiously to a cerebral blood vessel. Cerebral blood vessels include, but are not limited to, arteries such as the right and left anterior cerebral arteries, the right and left middle cerebral arteries, the right and left posterior communicating arteries, the right and left internal carotid arteries, portions of the right and left superior cerebellar arteries, portions of the left and right choroidal arteries, and smaller caliber vessels involved in collateral cerebral circulation, including, but not limited to, collateral vascular channels which are individually varied and un-named. Such delivery can be achieved by administering the composition intrathecally to the mammal.

One way to administer an NO donor compound to a human intrathecally comprises performing a ventriculostomy upon the mammal and delivering a solution of the NO donor compound via the ventriculostomy into a ventricle of the mammal's brain (e.g., the right lateral ventricle). Preferably, the solution is administered in aliquots of, for example, a few to about 5 milliliters. Immediately prior to injection, a volume of cerebrospinal fluid (CSF) which is equal to or slightly greater than the injected volume, should be withdrawn from the ventriculostomy, in order to avoid increasing the intracranial pressure (ICP) in the subject. Other vasodilating compounds can be administered in a similar fashion.

It is understood that subarachnoid delivery of a composition comprising an NO donor compound can be used to prevent or alleviate vasoconstriction or vasospasm in other cerebral arteries by delivering the composition to a subarachnoid space located geometrically closer to and in fluid communication with such other cerebral arteries. By way of example, delivery of such a composition to the (subarachnoid) cerebello-medullary cistern can be used to intrathecally administer the composition to blood vessels supplying the cerebellum, particularly the inferior aspect thereof. Similarly, vasoconstriction and vasospasm of arteries supplying the spinal cord can be prevented or alleviated by delivering a composition comprising an NO donor compound to the subarachnoid space geometrically close to a constricted or spastic spinal artery. The NO donor compound can be adventitially administered to a brain or spinal tissue using any known method of accessing the CSF of a patient including, but not limited to lumbar access to the subarachnoid space, ventriculostomy, or by needle access to the cisterna magna.

"Ventriculostomy" as used herein, refers to any known or hereafter developed method of providing access to a ventricle of a mammal's brain from outside the mammal's body. One method of ventriculostomy, for example, involves surgical placement of a device (i.e., the "ventriculostomy," such as a soft plastic cannula), following trephination of the mammal's skull, whereby the bore of the cannula is placed in fluid communication with both a ventricle of the mammal's brain and the extracorporeal environment.

An NO donor compound can also be intrathecally administered to a mammal using a more local route, for example, by subarachnoid catheter or intraoperatively, under the appropriate conditions of segmental vasospasm. For example, a plastic cannula can be inserted into the subarachnoid space surrounding the brain, without violating the brain itself, similar to the procedure involved in a ventriculostomy. This can be done at the time of surgery for aneurysm, or at a separate time by drilling the skull. NO donor compounds can also be intrathecally administered directly to cerebral surface blood vessels during surgery using a cannula.

In another preferred embodiment of the present invention, NO donor compound(s) is administered pericardially to cardiac blood vessels, such as the right and left coronary arteries. By way of example, a composition comprising SNP or one or more other NO donor compounds can be pericardially administered by inserting a needle in the fifth or sixth left intercostal space near the sternum, preferably under ultrasound or other visualization guidance, into the pericardium, and thereafter passing the composition through the bore of the needle into the pericardium. Alternately, the needle can be entered at the left costoxiphoid angle and passed upwards and backwards into the pericardial sac. In either case, caution should be taken to avoid violating the myocardium.

Other vasodilating agents with mechanisms of action similar to or different from that of NO can also be administered in accordance with the invention, although NO is the preferred agent. These agents can, for example, be introduced into the cerebrospinal fluid of a subject for treatment of cerebral ischemia attributable to substantially any cause (e.g., vasospasm, thromboembolic or hemorrhagic stroke, vasculitis, and chronic dementia) using the methods described herein. Some dementias and other neurological dysfunctions have an ischemic basis and can be prevented or alleviated by intrathecal administration of an NO donor compound, as those described herein. Chronic, rather than acute, forms of treatment is the preferred treatment paradigm for such circumstances, and appropriate means for introducing medications into the cerebral spinal fluid include the use of implanted reservoir and tubing systems, pumps, and other devices that can be accessed transdermally for intraventricular and intrathecal administration of medications or compounds described herein. Such medication is capable of either receptor activation from the adventitial side of the vascular wall, penetration of the vascular wall to activate receptors, or otherwise effecting local vasodilation by administration into cerebrospinal fluid or to another body compartment. An example of such a medication is adenosine, which is a potent vasodilator.

Typically, the amount of SNP to be administered to a human is in the range from about 10 to 88 milligrams per day in order to alleviate established vasoconstriction or vasospasm. More preferably, this dose range is from about 10 to 30 milligrams per day. This dosage should be administered in aliquots which should not contain more than about 5 to 12 milligrams of SNP, and the aliquots should be administered at least about 5 or 10 minutes apart. When administered as a prophylactic treatment for vasoconstriction or vasospasm, or when administered to dilate a non-constricted vessel, the typical amount of SNP should not exceed about 32 (and preferably about 24) milligrams per day for an adult human. More preferably, this dose range is from about 4 to 32 (preferably 4 to 12) milligrams per day. This amount should be administered in aliquots containing about 2 to 4 milligrams of SNP, and two aliquots should be administered 5 or 10 minutes apart, from one to three times per day (up to six aliquots per day or q.b.h.). Prophylactic treatment is preferably continued for at least about 10 days, and preferably not longer than about 21 days. Given the risk that concomitant hypotension may be induced as a result of treatment, the amount of NO donor compound to be used in each aliquot and the number of aliquots to be administered must be carefully monitored. The arterial blood pressure of the patient should also be monitored during treatment. Alterations in a prophylactic regimen can be guided by information obtained about an individual patient's condition or response to treatment, and such information can be obtained using non-invasive procedures such as transcranial Doppler ultrasound, magnetic resonance imaging (MRI), or Xenon computerized tomography (CT) scan. For example, if the prophylactic treatment does not appear to be enhancing peripheral blood flow in the desired region, the amount of NO donor compound administered to the patient can be increased. In a preferred embodiment, prophylactic treatment is preceded or accompanied by administration of an anti-emetic compound (e.g., ZOFRAN®). Furthermore, comparable dose ranges of NO donor compounds other than SNP can be deduced by the ordinary artisan by comparison of the anti-vasoconstriction or anti-vasospasm activity of the other compound with the corresponding activities of SNP.

Particularly contemplated in the invention is a composition comprising an amount of an NO donor compound which is suitable for delivery to a mammal in a single dose, wherein the single dose alleviates cerebrovascular spasm but does not induce systemic hypotension or intracranial hypertension. Such a dose is referred to herein as a "a single human intrathecal delivery amount" of an NO donor compound. The composition comprises an NO donor compound comprising at least one of NTG or SNP, or alternatively, the NO donor compound comprises L-arginine and an agonist of NO synthase. Suitable single dose amounts comprise about 0.5 to about 5 milligrams, and preferably about 4 milligrams, of NO donor compound in a volume of 5 milliliters of solution. When the single packaged dose of NO donor compound is in powdered form, a single dose can comprise about 0.5 to about 5 milligrams of NO donor compound which can be suspended in a volume of about 5 milliliters just prior to administration. It is also contemplated to include a single intrathecal delivery amount of an NO donor compound in one or more compartments of the drug delivery device described herein.

It is understood that the ordinarily skilled physician or veterinarian can readily determine and prescribe an effective amount of the NO donor compound to alleviate or prevent vasoconstriction or vasospasm or to dilate a blood vessel in the subject. In so proceeding, the physician or veterinarian can, for example, prescribe a relatively low dose at first, subsequently increasing the dose until an appropriate response is obtained. It is further understood, however, that the specific dose level for any particular subject will depend upon a variety of factors including the activity of the specific NO donor compound employed, the age, body weight, general health, gender, and diet of the subject, the time of administration, the route of administration, the rate of excretion, any drug combination, the anticipated rate at which the NO donor compound can be transported away from or degraded at the site of the blood vessel, and the severity and duration of the vasospasm or vasoconstriction being alleviated or prevented.

The amount of the NO donor compound or other vasodilating compound and the formulation in which it is administered will vary based on the location and nature of the tissue in or on which the blood vessel to which the compound is to be adventitially administered occurs. For example, where significant fluid flow is anticipated past a tissue (e.g., within the lumen of the bladder, on the exterior surface of a peritoneal organ, or on a synovial surface of a cartilage), it can be preferable to use a formulation that is not significantly dissipated by fluid flow, or to inject the compound into the tissue. Further by way of example, when the site at which the compound is to be administered is located at a distance from the adventitial surface of a target blood vessel (e.g., a ventriculostomy site located several millimeters to several centimeters from the adventitial surface of a cerebral blood vessel), it can be beneficial to formulate the compound in a fluid that can diffuse or flow from the site of administration to the intended site of action. An estimate of an effective amount of a compound can be obtained using an accepted model of the body system to be targeted by administration of the compound. Many such models are known, no non-human animal being considered an acceptable model for all systems. Furthermore, it is an accepted practice for a clinician to first administer a relatively low amount of a compound and observe a patient's response prior to administering a larger dose, and this practice can be used to determine a suitable dose for a patient.

Prior to administration of an NO donor compound to a mammal, the donor can be formulated in a pharmaceutically acceptable carrier such as, but not limited to, sterile physiological saline. However, a preferred formulation is a powdered form of the NO donor compound which can be suspended or dissolved in a solution comprising the patient's own CSF or a synthetic CSF solution, such as that described herein. Other appropriate solutions include normal saline (0.9% w/v) or a 5% (w/v) dextrose solution.

In a preferred embodiment of the methods of the invention, one or more NO donor compounds are administered in the form of a sustained-release formulation, wherein at least a portion of the compound is not contacted with the physiological environment in the mammal immediately upon administration of the formulation to the mammal. Preferably, the NO donor compound(s) is released from the formulation into the physiological environment over a period of minutes, hours, days, or even weeks. Numerous sustained-release formulations of active pharmaceutical agents such as NO donor compounds are known in the art, and a full discussion of such formulations is not presented here. By way of example, such compositions include slow-dissolving or biodegradable solid or polymeric compositions, oily suspensions, and oil-in-water, water-in-oil, and other emulsions. These compositions can contain the compound mixed more or less homogeneously throughout the composition, or they can include granules, vesicles, layers, pockets, or other discrete regions in which the agent is concentrated or contained. The compound can be provided in a form that is metabolically inactive when introduced to the mammal, and that can be converted to its active form upon interaction with a second agent which is delivered by the same or an alternative route of administration as the compound (e.g., systemic, intrathecal, intravascular, and transcutaneous) for example, upon activation by transcutaneously-delivered ultraviolet light.

The compound can be provided in a metabolically-inactive form that is introduced outside the central nervous system compartment (e.g., intravenously) and is converted to an activated form by metabolic activity that occurs in one or more anatomical regions of the central nervous system upon introduction of another agent in a selective manner (e.g., intrathecal or intravascular administration of a compound, or transcutaneous application of an energy agent such as ultraviolet light) to the central nervous system or to a portion thereof. This method of local metabolic activation can be applied to other body regions or compartments where use of an NO donor compound to inhibit, prevent, or alleviate vasoconstriction or vasospasm is desired. Localized induction of NO generating activity can also be achieved by local delivery of a nucleic acid vector encoding an enzyme that catalyzes NO generation to the site.

Administration of NO donor compounds such as SNP can potentially release harmful cyanide or cyanate moieties into the mammal or otherwise cause the mammal to experience nausea. Thus, in another preferred embodiment of the compositions and methods of the invention, the NO donor compound is administered in conjunction with a cyanide or cyanate scavenger such as hydroxycobalamin, thiosulfate, or any other scavenger that will remove, chelate, bind, inactivate, or otherwise render cyanide compounds and derivatives thereof non-harmful. Alternatively, NO donor compounds such as SNP can be administered in a formulation that includes both the NO donor compound and one or more agents, such as hydroxycobalamin or thiosulfate, that remove, chelate, or otherwise inactivate cyanate or cyanide-containing byproducts of metabolism of SNP. The NO donor compound can be administered before, after, or in conjunction with an anti-emetic to alleviate, prevent, or inhibit nausea which can be associated with administration of the NO donor compound, with an anti-inflammatory compound to reduce or alleviate inflammation associated with the treatment methods described herein, with an oxyhemoglobin-reducing compound (e.g., sodium nitrite) to minimize the amount of oxyhemoglobin in the subarachnoid (or other) body location to which the composition is administered, with a thrombolytic agent to minimize or alleviate blood clotting which can exist or which can occur at the body location to which the composition is administered, or with an antibiotic compound to minimize or alleviate microbial contamination which may exist or which may be introduced at the body location to which the composition is administered.

As used herein, a first compound is administered "in conjunction" with a second compound if the first and second compounds are administered at times such that the periods during which the physiological effects of the two compounds are manifested overlap. Thus, the first compound can be administered before, after, or at the same time as the second compound. Where the second compound is administered in order to alleviate, prevent, or counteract an undesirable physiological effect of the first compound, then the second compound is preferably administered in a manner, in an amount, and at one or more times, such that the physiological effect of the second compound is manifested during the entire period during which the physiological effect of the first compound is manifested.

The NO donor compound can be formulated in a pharmacologically acceptable carrier and is preferably packaged as a single dose in a sealed ampoule or a sealed syringe or other sealed device. A device useful for the purpose of intrathecal administration of an NO donor compound to a human is described herein, including in Example 3. The single dose package of an NO donor compound can be in solution provided it is used shortly after packaging and provided the NO donor compound is protected from light while so packaged. Alternatively, as described herein, the single dose of an NO donor compound is packaged in powder form and is re-suspended in the patient's own CSF just prior to administration.

The NO donor compound can be administered to a blood vessel which is not constricted or spastic, although the vasodilation which is thereby achieved is understood to be smaller in magnitude. Of course, prophylactic treatment of vasoconstriction, vasospasm, disturbance or obstruction of peripheral circulation, and other ischemic conditions comprises adventitially administering such a compound to one or more blood vessels which may or may not be constricted or spastic.

The invention encompasses the preparation and use of pharmaceutical compositions comprising an NO donor compound as an active ingredient. Such a pharmaceutical composition can consist of the active ingredient alone, in a form suitable for administration to a subject, or the pharmaceutical composition can comprise the active ingredient and one or more pharmaceutically acceptable carriers, one or more additional ingredients, or some combination of these. Administration of one of these pharmaceutical compositions to a subject is useful for preventing or alleviating vasoconstriction or vasospasm or for dilating a blood vessel in the subject, as described elsewhere in the present disclosure. The active ingredient can be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient can be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered, and which does not prevent the NO donor compound from generating NO in vivo.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition can comprise between 0.1 % and 100% (w/w) active ingredient.

In addition to the active ingredient, a pharmaceutical composition of the invention can further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pregelatinized maize starch, polyvinylpyrrolidone, and hydroxypropyl methylcellulose. Known lubricating agents include, but are not limited to, magnesium stearate, stearic acid, silica, and talc.

Tablets can be non-coated or they can be coated using known methods to achieve delayed disintegration in the gastrointestinal tract of a subject, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin.

Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition of the invention can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the invention can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

Retention enema preparations or solutions for rectal or colonic irrigation can be made by combining the active ingredient with a pharmaceutically acceptable liquid carrier. As is well known in the art, enema preparations can be administered using, and can be packaged within, a delivery device adapted to the rectal anatomy of the subject. Enema preparations can further comprise various additional ingredients including, but not limited to, antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation can be made by combining the active ingredient with a pharmaceutically acceptable liquid carrier. As is well known in the art, douche preparations can be administered using, and can be packaged within, a delivery device adapted to the vaginal anatomy of the subject. Douche preparations can further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue, so long as the NO donor compound is not administered systemically. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations can, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e., by rapid inhalation through the nasal passage from a container of the powder held close to the nares.

Formulations suitable for nasal administration can, for example, comprise from about as little as 0.1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations can, for example, be in the form of tablets or lozenges made using conventional methods, and can, for example, 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition of the invention can be prepared, packaged, or sold in a formulation suitable for ophthalmic administration. Such formulations can, for example, be in the form of eye drops including, for example, a 0.1–1.0% (w/w) solution or suspension of the active ingredient in an aqueous or oily liquid carrier. Such drops can further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which can be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The invention also includes a device for delivering to a mammal a pharmacologic agent having a short half-life in solution, such as an NO donor compound (e.g., SNP). Numerous pharmaceutically active compounds degrade, decompose, or otherwise react with aqueous solutions in a way which causes them to be no longer pharmaceutically active. The short half-life of these compounds can have resulted in their not being used clinically, particularly when the compounds have their pharmacological effect at body locations which can only be accessed following difficult or cumbersome surgical procedures. This device of the invention is useful for administration of such short-lived agents to a body location, such as a body cavity or a body fluid, because the device can be used to deliver the agents to the appropriate location minutes, seconds, or even within a second (depending upon the solubility of the agent in the solvent used with the device and upon whether the agent can be delivered as a suspension or only as a solution) after solvating the agent.

The device employs two chambers having a fluid connection therebetween. A first chamber is used to draw up, to store, or to otherwise contain a solvent in which the pharmacological agent is to be dissolved or suspended prior to administration of the agent to a mammal. The second chamber contains the agent. The agent can be added to the second chamber before or after the solvent is provided to the first chamber. When the agent decomposes, reacts, or otherwise unfavorably reacts or with aqueous solutions (e.g., when the agent is SNP), the agent is preferably provided in the second chamber in a substantially anhydrous form. For example, the device can be provided as a disposable unit which does not contain solvent, but which contains the agent in the second chamber, preferably in a unit dose form. It is important that the interior portions of the device (i.e., the two chambers and any fluid conduits connecting them) be maintained in a sterile condition prior to use of the device in the methods of the invention, lest use of the device introduce microbial or other contamination into the body of the mammal. The device is operated by drawing a body fluid into the first chamber, passing the fluid through the fluid conduit to the second chamber, and mixing the fluid with the agent in the second chamber. The fluid-mixed agent can then be delivered to the mammal, either directly from the second chamber, or by passing the fluid-mixed agent through the fluid conduit to the first chamber and thence into the mammal.

In a preferred embodiment of the invention, the device is adapted for intrathecal administration of the NO donor compound to the mammal. The device is adapted to be capable of withdrawing a selected volume of CSF from the patient. The device comprises a first chamber for receiving the CSF and a second chamber which contains the NO donor compound and into which the withdrawn CSF can be passed without disassembling the device. Preferably, the first and second chambers are in fluid communication with one another (although a closeable valve, a pump, or the like can optionally be interposed between the two chambers), such as by means of a fluid conduit extending between the two chambers or, if the two chambers have a common wall, an orifice in the wall. The second chamber can be openable, whereby the user can deposit the NO donor compound therein or, preferably, the device is supplied with the NO donor compound already present in the second chamber. Once the CSF is transferred from the first to the second chamber, the CSF is mixed with the NO donor compound, whereby the compound is dissolved, suspended, or both, in the CSF. The CSF containing the NO donor compound is then delivered into a subarachnoid space of the patient, such as a brain ventricle (e.g., the third ventricle), either by expelling the CSF from the second chamber into the subarachnoid space, or by transferring the CSF from the second chamber to the first and thence into the subarachnoid space. Preferably, the device is a disposable device for one-time use and is pre-loaded with a pre-determined mount of an NO donor compound.

In another preferred embodiment, the device comprises
1) a first hollow body having a flow orifice, a first fluid access port, and a first pressure orifice, each in fluid communication with the interior of the first hollow body;
2) a second hollow body for containing the pharmacological agent, the second body having a second fluid access port in fluid communication with the interior of the second hollow body and in fluid communication with the first fluid access port, and an outlet port in fluid communication with the interior of the second hollow body; and
3) a first pressure modulator connected to the first pressure orifice. The first and second hollow bodies can, for example, be separate syringes, two chambers of a multi-chamber syringe, a specially-constructed device such as that illustrated in FIG. 7, separate plastic or glass vials, separate portions of a material having a plurality of cavities, or the like. The pressure modulator connected to the first pressure orifice can be substantially any mechanism which can be used to modulate gas or liquid pressure (e.g., a gas or liquid pump, an elastomeric bulb, a plunger, a cotton-plug port for oral aspiration, etc.). Preferably, the first pressure modulator is a plunger which is snugly slidably disposed within the interior of the first hollow body, meaning that when the plunger is actuated, sliding the plunger causes a change in pressure in the interior of the hollow body, as is well known (e.g., traditional syringe plungers are snugly slidably disposed within the barrel of the syringe). Also preferably, a second plunger is snugly slidably disposed within the interior of the second hollow body, for controlling fluid flow into and out of the interior thereof. The device can also have an adapter at the flow orifice of the first hollow body, for connecting the device to a fluid handling device such as an infusion line or a CSF drainage.

A plunger is "snugly" slidably disposed within a cavity if the plunger can be actuated along the long axis of the cavity and if, upon actuation, the plunger is able to maintain a pressure differential within the cavity on the two sides of the plunger of at least about 0.1 atmosphere (gauge), and preferably at least about 0.5 or 1.0 atmosphere (gauge).

A fluid (e.g., a body fluid such as CSF or a solution not obtained from an animal such as synthetic CSF) is drawn into the interior of the first hollow body through the flow orifice by operation of the first pressure modulator, which is used to reduce the pressure within the first hollow body, thereby drawing the fluid in. The fluid flows to the interior of the second hollow body by flowing through the first fluid access port, optionally through a fluid conduit which connects the first and second fluid access ports, and through the second fluid access port. The fluid can be caused to flow into the second chamber by gravity or by actuating a second pressure modulator adapted to the interior of the second hollow body, for example. In the interior of the second hollow body, the fluid is mixed with the pharmacological agent. After mixing, the fluid-mixed agent flows from the interior of the second hollow body through the outlet port. The fluid-mixed agent can be caused to flow from the interior of the second hollow body by gravity or by actuating a second pressure modulator (e.g., a plunger) adapted to the interior of the second hollow body. The outlet port and the second fluid access port can be the same orifice, in which case the fluid is returned to the interior of the first hollow body after mixing. If the outlet port and the second fluid access port are not the same port, then the outlet port can be in fluid communication with the interior of the first hollow body, or it can be used to deliver the mixed fluid directly to the mammal. After mixing, the fluid is administered to the animal, either by way of the flow orifice of the first hollow body or the outlet port of the second hollow body.

Preferably, according to the preceding embodiment, the device further comprises a valve having an outlet orifice and an inlet orifice which is coupled to the outlet port of the second hollow body and the outlet port and the second fluid access port are not the same port. The valve permits fluid flow only in the direction from the inlet orifice to the outlet orifice. The valve serves to prevent fluid from flowing through the outlet port of the second hollow body into the interior of the second hollow body, but permits flow from the interior of the second hollow body through the outlet port. Numerous one-way valves are known in the art and can be coupled to an outlet port using a variety of known methods.

In one embodiment, the device comprises two syringes and a three-way valve. The valve is connected to the first syringe, the second syringe, and to a fluid conduit which is in fluid communication with a body fluid of a mammal (e.g., a three-way valve connected to two syringes and to an emplaced ventriculostomy). The three-way valve selectably connects any two of the first syringe, the second syringe and the fluid conduit. This device is used as follows. The three-way valve is selected to connect the fluid conduit and the first syringe, and the body fluid is taken up in the first syringe. The three-way valve is then selected to connect the two syringes. The second syringe contains a pharmacological agent to be delivered to the mammal by way of the body fluid. The fluid in the first syringe is transferred, by way of valve, to the second syringe, where the fluid is mixed with the agent, dissolving or suspending the agent in the fluid. The three-way valve is then selected to connect the second syringe with either the fluid conduit or the first syringe, and the contents of the second syringe are expelled. If the second syringe was connected to the fluid conduit, the fluid-mixed agent is delivered to the mammal, and any fluid-mixed agent which remains in the fluid conduit can be flushed therefrom by selecting the valve to connect the first syringe and the fluid conduit and thereafter expelling liquid from the first syringe. If the second syringe was connected to the first syringe, the fluid-mixed agent is delivered to the first syringe, wherein it is diluted with any fluid in the first syringe. The valve is then selected to connect the first syringe and the fluid conduit, and the diluted fluid-mixed agent is administered to the mammal.

In an optional embodiment, the first syringe is replaced with a fluid reservoir. In this embodiment, fluid is drawn from the fluid reservoir into the second syringe and mixed therein with the agent. The fluid-mixed agent is then expelled from the second syringe, either into the fluid reservoir or, preferably, into the fluid conduit. The fluid reservoir is then connected to the fluid reservoir to flush the fluid-mixed agent from the conduit, to supply liquid to the mammal, or both.

In another optional embodiment, the valve is a four-way valve which is also connected to a fluid reservoir. The valve can connect the fluid conduit and the fluid reservoir;
the fluid reservoir and the first syringe;
the first syringe and the second syringe; or
the second syringe and the fluid conduit.

Instead of drawing body fluid from the mammal, the first syringe draws fluid from the fluid reservoir. The fluid is transferred to the second syringe, wherein it is mixed with the pharmacological agent. The fluid-mixed agent is delivered to the mammal by expelling the fluid-mixed agent from the second syringe through the fluid conduit. Optionally, the fluid reservoir is thereafter connected with the fluid conduit to provide fluid to the mammal.

As used herein, a "fluid mixed agent" is an agent mixed with a fluid, and can comprise a solution of the agent in the fluid, a suspension of the agent in the fluid, or both.

A fluid, chamber, tissue, or body location is "in fluid communication" with another fluid, chamber, tissue, or body location if a fluid present at the location of the first is able to flow to the location of the second.

In another embodiment, the device comprises one or more compartments which contain pre-selected amounts of the NO donor compound and which are separated from the second chamber by a breachable barrier, such as a scored or perforated polymeric or non-polymeric film or foil. A plunger slidably disposed within each chamber, for example, can be actuated to breach the barrier and to either expel the pre-selected amount of the compound into the second chamber or place the compound in fluid communication with the second chamber. Alternately, the compartment(s) can be deformable (e.g., a deformable plastic bubble), and the composition contained within the compartment can be delivered to the second chamber by deforming the chamber to the extent that the composition is forced through the breachable barrier. Regardless of the mechanism employed to permit delivery of the composition from the compartment(s) to the second chamber, it is important that the second chamber (as well as the first chamber) remain isolated from the environment (i.e., impervious to external contamination), in order to preserve the sterility of the first and second chambers, at least until the CSF containing the NO donor compound is administered to the patient.

In one embodiment, the device renders withdrawal of a certain volume of CSF necessary prior to delivery of the pharmacologic agent while simultaneously limiting the amount of the agent that can be administered at one time. The device therefore provides a margin of safety that is helpful under the circumstances of intrathecal drug delivery, such as brain ischemia, elevated intracranial pressure and systemic hypotension. The requirement that a certain volume of CSF be withdrawn prior to delivery of the agent results from the placement of the fluid connection between the first and second chambers and the use of a plunger to withdraw the CSF. The fluid connection is situated within the first chamber such that the CSF fluid cannot flow through the connection until the plunger has been withdrawn to a position at which the certain volume of CSF has been withdrawn. The limitation of the amount of the agent that can be administered at once results from the presence within the second chamber, or within a compartment separated from the second chamber by a breachable barrier, of a the selected amount of the NO donor compound.

As noted herein, the device is suitable for the intrathecal administration of an NO donor compound to a mammal. However, it will be appreciated that the device is not limited solely to the administration of an NO donor compound. Rather, other pharmacological agents can be delivered intrathecally to a mammal using the device of the invention. Such other agents include, but are not limited to, antibiotics, chemotherapy agents, oxygen-carrying fluid compounds, antibodies, particularly monoclonal antibodies, thrombolytic agents, steroids, osmotic agents, anti-emetics, anti-inflammatory agents, oxyhemoglobin-reducing agents, and papaverine. Furthermore, the device can be used to withdraw substantially any body fluid from a mammal in a sterile manner, dissolve a pharmacological agent in the fluid, and return the fluid to the mammal. Of course, where the body fluid is blood, the agent is preferably not an NO donor compound, which can induce systemic hypotension if administered systemically.

The advantages of the device are as follows. The device maintains sterility of the body fluid. For example, the device can be sterilized (including the pharmacological agent to be delivered) prior to coupling the device with a fluid handling device (e.g., a needle, a CSF drainage, or the like). Because the device is closed (i.e., the interior of the device is separated from the environment outside the animal's body), the body fluid can be withdrawn, the agent mixed with the body fluid, and the body fluid returned to the animal's body without exposing the body fluid to the environment outside the animal's body, thereby avoiding potential contamination of the body fluid and corresponding complications resulting therefrom. Where the device is used for intrathecal administration of an agent, the device can be employed to require withdrawal of the patient's CSF in a volume at least equal to the volume of fluid to be delivered, thereby preventing potentially harmful increases in ICP and permitting modulation of ICP, which are important safety considerations in the delivery of agents by the intrathecal route of administration. In addition, the device can be employed to require delivery of the pharmacologic agent in a predetermined limited dosage.

The materials and methods used to construct the device are not critical. Any suitable materials can be used, as will be apparent to one skilled in the art in view of the present disclosure, including, but not limited to, glass, plastics, metals, and the like. Likewise, various methods by which the device can be synthesized will be apparent to the skilled artisan in view of the present disclosure. When the agent to be delivered using the device (e.g., SNP) is light-sensitive, at least a portion of the second hollow body, at least a portion of a compartment separated from the interior of the second hollow body, or both, are preferably partially or wholly opaque.

The invention also includes a subdural insertional guide having a substantially rigid body and a lumen within the body. The body has a long axis, a proximal end, a distal end, and an outer surface. The lumen extends from the proximal end of the body, through the body, to the external surface of the body. At the proximal end, the axis of the lumen is substantially parallel to, and preferably co-axial with, the long axis of the body. At the external surface of the body, the axis of the lumen is substantially perpendicular to the long axis of the body. Thus, the lumen makes at least an approximately 90 degree turn within the body. This feature diminishes the risk associated with placement of a subdural catheter by reducing the likelihood of brain penetration by the catheter and by permitting simple perpendicular trephination of the skull using a relatively small hole. The use of a small hole is preferable in both angled trephination (or drilling) and in making a larger bony opening. Once trephination is performed, the dura mater is surgically opened in the usual fashion and the distal end of the device is inserted through the dural opening. The distal end of the device is preferably relatively broad and can be used to gently depress the brain tissue at the trephination site by urging the guide distally against the brain tissue. Optionally, the subdural insertional guide has an inflatable balloon (e.g., a circumferential balloon).

The use of the balloon serves to effectively increase the diameter of the base to a safe width for depressing brain tissue and permits minimization of the diameter of the guide, and thus of the trephination. Upon gentle depression of the brain tissue, a subdural (or intradural) catheter can be introduced through the trephination site by urging the catheter through the lumen of the guide. The device can be used for the introduction of therapeutic compounds to the brain of a human, as described elsewhere herein. Alternatively, this device can be used to introduce a fiber optic illumination and visualization system for therapeutic or diagnostic purposes, or as a preliminary step to the introduction of a catheter.

The invention further includes a subdural catheter comprising a soft, generally tubular body for evenly distributing a fluid to an exterior surface or to an interior surface (i.e., a surface facing a ventricle) of the brain of a mammal. The catheter comprises a material which is soft, flexible, and, preferably, at least partially radio-opaque (e.g., barium impregnated). The catheter has an outer surface, a proximal end, a distal end, and a lumen extending within the body from the proximal end thereof. The catheter has a hub at the proximal end thereof for connecting the catheter to a fluid handling device such as a syringe, an infusion line, or the device of the invention. The hub can be integral with the body of the catheter, or it can be attached thereto. The catheter has one or more, and preferably many, holes extending from the lumen to the outer surface of the body. Preferably, many or most of the holes are located nearer the distal end of the body than the proximal end. Also preferably, the body has a flattened cylindrical shape. Fluid or liquid medication is delivered to the device through the hub. The fluid or medication then travels through the lumen of the catheter and subsequently passes from the lumen through the hole(s) to the environment surrounding the catheter. The lumen is optionally inversely tapered from the proximal to the distal end thereof, i.e., it gradually widens toward the end of the catheter furthest from the hub. This design permits improves distribution of the fluid from the catheter.

The invention also includes a kit for dilating a constricted or spastic blood vessel in a mammal. This kit comprises an NO donor compound and an instructional material which describes adventitially administering this compound to a blood vessel of the mammal. In another embodiment, this kit comprises a (preferably sterile) solvent suitable for dissolving or suspending the NO donor compound prior to administering the compound to the mammal.

As used herein, an "instructional material" includes a publication, a recording, a diagram, or any other medium of expression which can be used to communicate the usefulness of the NO donor compound of the kit for dilating a constricted or spastic blood vessel in a mammal, or for alleviating or preventing vasoconstriction or vasospasm. Optionally, or alternately, the instructional material can describe one or more methods of adventitially administering the NO donor compound to a blood vessel of a mammal. The instructional material of the kit of the invention can, for example, be affixed to a container which contains the NO donor compound or be shipped together with a container which contains the compound. Alternatively, the instructional material can be shipped separately from the container with the intention that the instructional material and the compound be used cooperatively by the recipient.

The invention further includes a kit for intrathecal administration of an NO donor compound to a mammal. This kit comprises the device of the invention and an instructional material which describes using the device to intrathecally administer the compound to a mammal. The device is preferably supplied in a sterile, sealed package, and preferably comprises an adapter at the flow orifice thereof which is suitable for attaching the device to a fluid handling device, such as a CSF drainage line. The kit preferably further comprises the NO donor compound, supplied in a bulk form, in unit dosage form, or, more preferably, contained within the interior of the second hollow body of the device. In another embodiment, this kit comprises a (preferably sterile) solvent suitable for dissolving or suspending the NO donor compound prior to administering the compound to the mammal.

The invention still further comprises a subdural catheterization kit. This kit comprises at least one subdural catheter of the invention and at least one subdural insertional guide. Preferably, this kit further comprises an instructional material which describes use of the subdural insertional guide for placement of the subdural catheter of the kit. The kit can also comprise one or more of an NO donor compound, the device of the invention, and a (preferably sterile) solvent suitable for dissolving or suspending the NO donor compound prior to administering the compound to the mammal.

EXAMPLES

The invention is further described in detail by reference to the following experimental examples. These examples are provided for purposes of illustration only, and are not intended to be limiting unless otherwise specified. Thus, the invention should in no way be construed as being limited by the following examples, but rather, should be construed to encompass any and all variations which become evident as a result of the teaching provided herein.

Example 1

Rapid Reversal of Endothelin-1-Induced Cerebral Vasoconstriction by Intrathecal Administration of Nitric Oxide Donor Compounds The experiments described herein establish that NO donor compounds, such as sodium nitroprusside (SNP) and nitroglycerine (NTG), which are delivered to the adventitial side of the blood vessel in the cerebrospinal fluid (CSF), induce reversal of cerebral vasoconstriction without inducing systemic hypotension.

An animal model of induced vasospasm was used in which direct visual observation of a cerebral blood vessel in vivo was possible.

Experimental Animals

Fifty male New Zealand White rabbits weighing 1.5–2.5 kilograms were used in the study. Eight animals were used as pure SNP or NTG controls. The remaining animals were used in vasospasm reversal experiments. All procedures were reviewed and approved by the Animal Research Ethics Committee of the University of Southern California.

Anesthetic Preparation

Anesthesia induction was accomplished using Ketamine (40 milligrams per kilogram body weight) and Xylazine (6 milligrams per kilogram body weight). Following satisfactory anesthesia the animals were endotracheally intubated and general anesthetic agents were administered (halothane 1% (v/v), nitrous oxide at 1 liter per minute and oxygen at 1 liter per minute). Oxygen saturation was maintained greater than 95% as assessed by pulse oximetry. A femoral arterial line was placed for continuous blood pressure monitoring and an ear vein intravenous line was placed for the continuous administration of physiologic saline solution. Arterial blood gases were sampled every 15 minutes.

Surgical Procedure

When anesthesia was accomplished, the subject was placed supine on the operating table and a transcervical-transclival approach to the brainstem and basilar artery was performed under microscopy. The dura and arachnoid coverings were opened sharply following removal of approximately 1.0×1.5 centimeters of bone of the skull base with a high speed drill. Any direct or indirect contact with or mechanical disturbance of the basilar artery or its branches was meticulously avoided, and any such disturbance resulted in removal of that subject from the study.

Experimental Drugs and Their Administration

The following experimental substances were used in the present study. Endothelin-1 (Peninsula Laboratories Inc., Belmont, Calif., USA); sodium nitroprusside (SNP; Elkins-Sinn Colo., Cherry Hill, N.J., USA); nitroglycerine (NTG; Solopak Laboratories, Inc., Elk Grove, Ill., USA). All experimental substances were delivered in the medium of synthetic cerebrospinal fluid (sCSF) at 37° C. The composition of sCSF was as follows: 124 millimolar NaCl, 3.30 millimolar KCl, 1.25 millimolar $KH_2PO_4$, 2.40 millimolar $MgSO_4$, 2.00 millimolar $CaCl_2$, 25.70 millimolar $NaHCO_3$, and 10 millimolar glucose.

Experimental Procedure

Continuous irrigation of the exposed brainstem and basilar artery with sCSF was begun upon arachnoid removal through a delivery catheter calibrated to deliver at 1.0 milliliter per minute. All experimental substances were delivered in this medium. Fluid was simultaneously removed through a catheter at the opposite pole of the field at a constant rate, so that the fluid level over the artery was maintained at the same depth throughout the procedure. The dimensions of the basilar artery were constantly observed and measured by video microscopy and an in-line calibrated video caliper. Magnification (f=200) and zoom factor (factor=2,0) were maintained constant throughout all experiments.

The basilar artery was initially observed for twenty minutes until a stable baseline measurement of its diameter was assured. After this, the experimental substance was delivered at a constant rate. In the present study, 3 control groups (n=8) and 3 experimental groups (n=38) of animals were used. Control groups were used to evaluate the possible effect of pure sCSF and sCSF containing SNP or NTG delivered at a rate of 2 milligrams/milliliters per minute. The first experimental group (n=15) received sCSF with ET-1 (100 nanomolar, administered at a rate of 1 milliliter per minute). When maximum vasoconstriction was considered to be present, the ET-1 suffusion was stopped and replaced by sCSF alone until the diameter of the basilar artery returned to the baseline. The second (n=13) and third (n=10) experimental groups received the suffusion of SNP or NTG (2 milligrams per milliliter) following the maximal vasoconstriction induced by ET-1. The results were subjected to ANOVA followed by Bartlett's test. Comparisons between the effects of ET-1 and ET-1 followed by NTG or SNP were made using Student-Newman-Keuls Multiple Comparison Test. A P value <0.05 was considered significant.

Figure 1B:
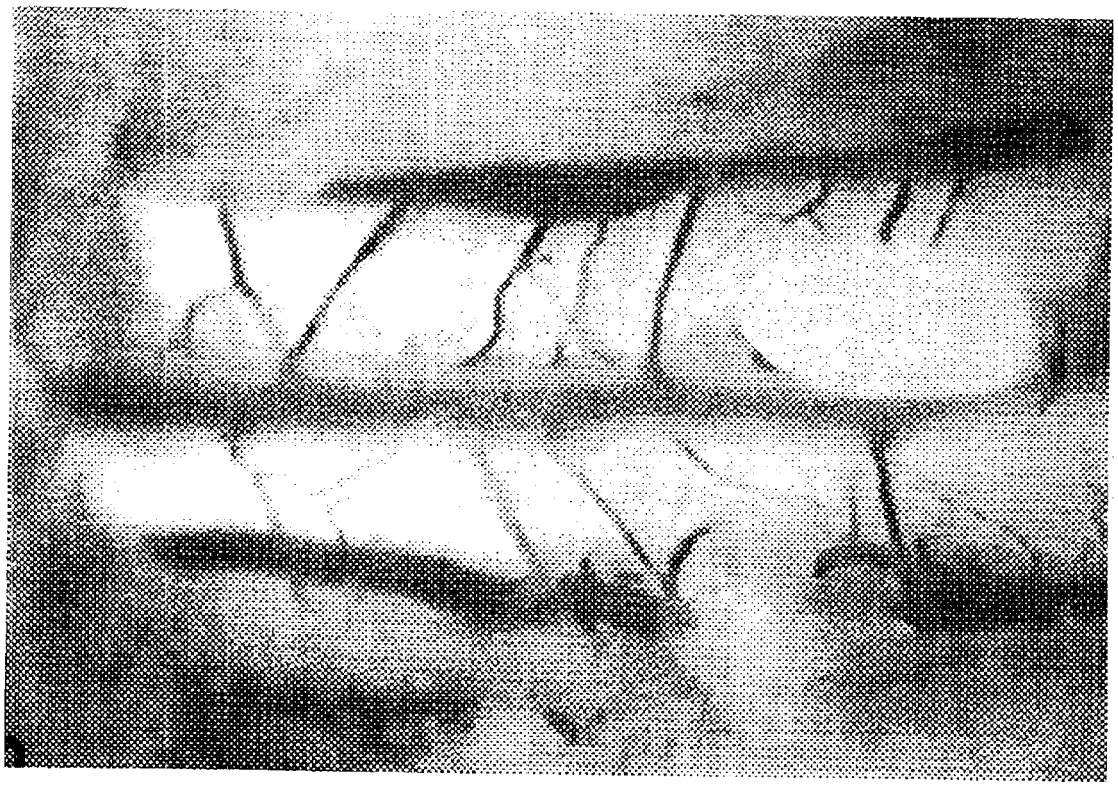

The range of baseline arterial diameters was 992 microns±the standard deviation. No significant change in arterial diameter occurred in animals exposed to sCSF alone (Group 1). Administration of ET-1 resulted in reduction of arterial diameter which began 5–8 minutes after starting the delivery and was complete within 20–30 minutes (Groups 4, 5, 6; n=38). The average minimal diameter of the artery was 500 microns (50.4% of baseline diameter). Further vasoconstriction was never observed after 30 minutes of suffusion (FIG. 1). This experiment is tabulated in Table 1.

TABLE 1

| Group # | 1 | 2 | 3 | 4 | 5 | 6 |
|---|---|---|---|---|---|---|
| Substance Suffused (in sCSF) | sCSF | SNP | NTG | ET-1/sCSF | ET-1/SNP | ET-1/NTG |
| n | 3 | 3 | 3 | 15 | 13 | 10 |

Figure 2A:
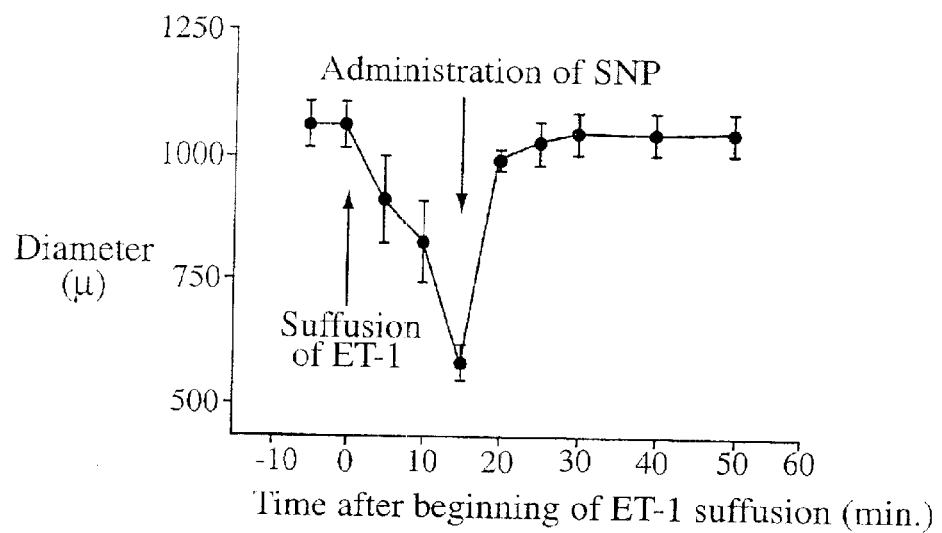
FIGS. 2A and 2B, is a graph (FIG. 2A) and an image (FIG. 2B) depicting the effect of sodium nitroprusside (SNP) on vasoconstriction induced by ET-1.
Figure 2B:
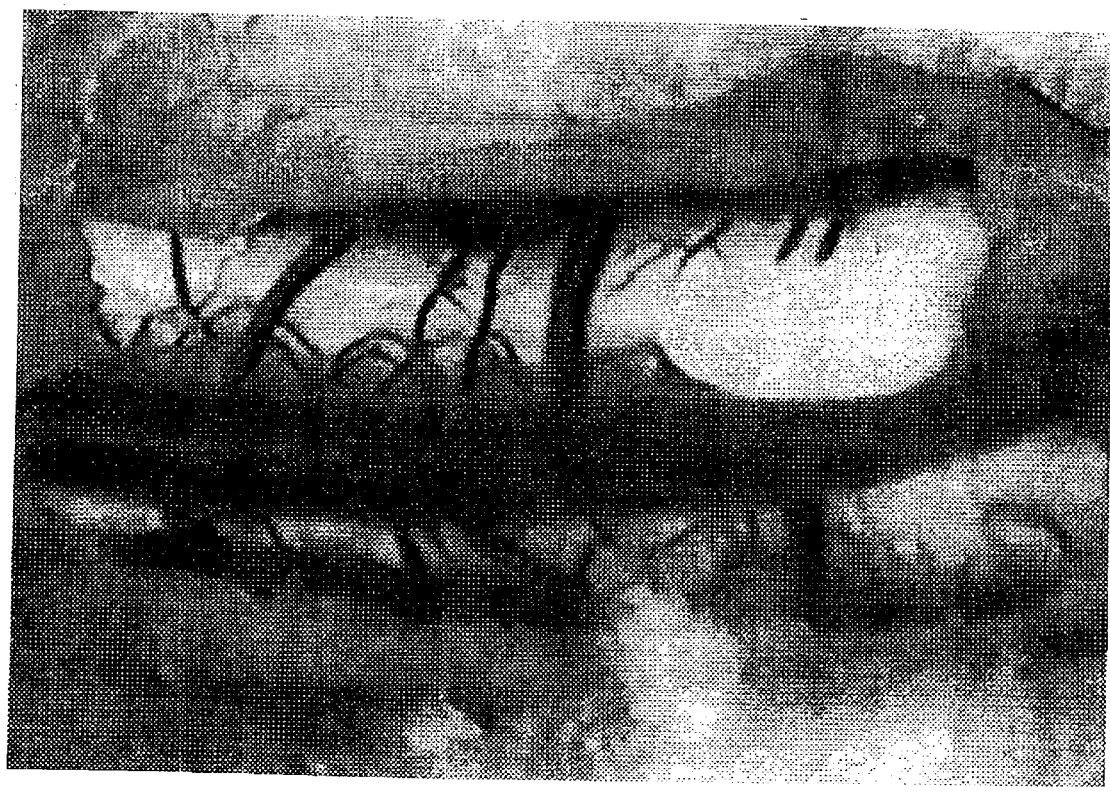

Administration of sCSF alone following ET-1 (Group 4, n=15) resulted in a very prolonged return to baseline (>30 minutes). Administration of SNP-sCSF (Group 2, n=3) alone did not produce significant changes in the diameter of the basilar artery within 60 minutes of observation. Administration of SNP-sCSF (Group 5, n=13) at the time of maximal vasoconstriction by ET-1 rapidly and completely reversed vasoconstriction. Return to baseline diameter was observed within several minutes in all cases. This effect was sustained for the duration of the procedure, without signs of constriction after 30 minutes (FIG. 2).

Figure 3:
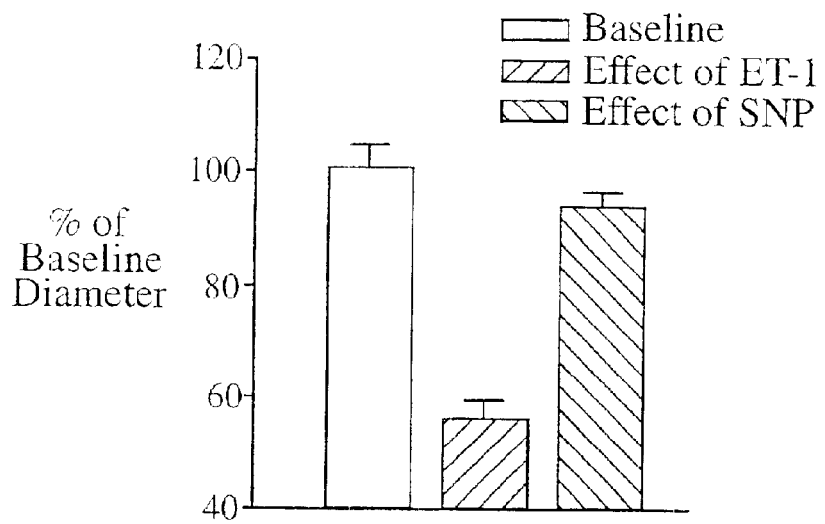
FIG. 3 is a graph depicting the effect of ET-1 and SNP on basilar artery diameter.
Figure 4:
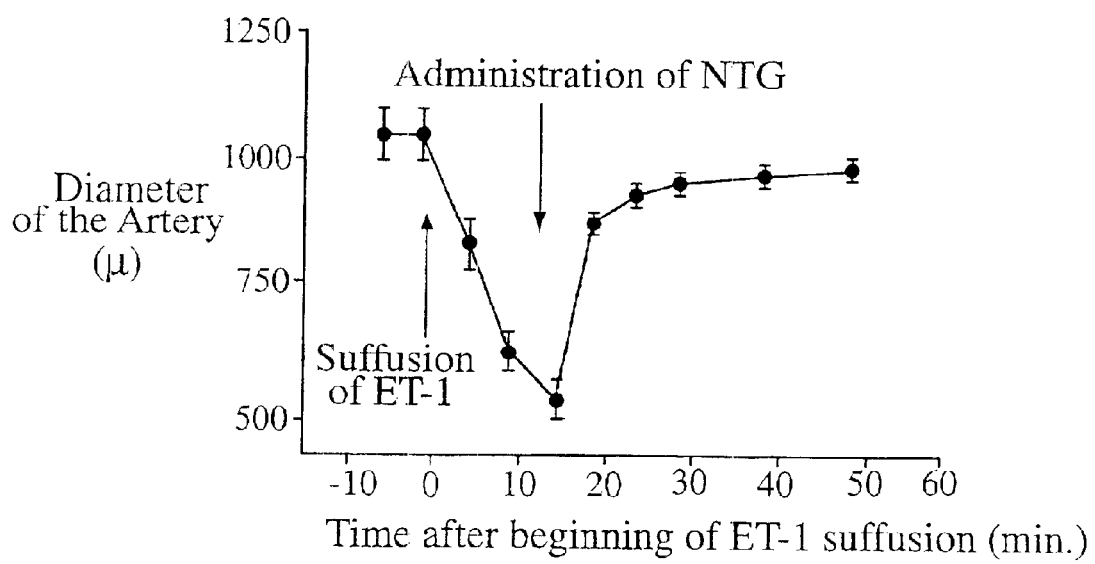
FIG. 4 is a graph depicting the effect of NTG on vasoconstriction induced by ET-1.
Figure 5:
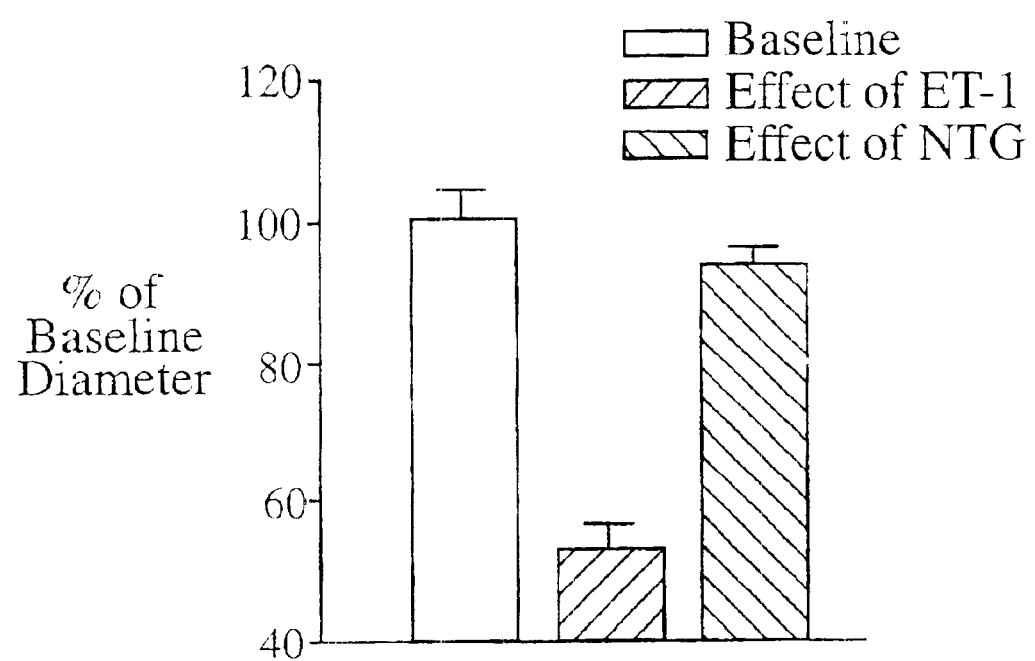
FIG. 5 is a graph depicting the effect of ET-1 and NTG on basilar artery diameter.

Similar results were obtained with NTG. Suffusion of NTG-sCSF (Group 3, n=3) did not produce changes in the baseline diameter of the artery. However, administration of NTG after ET-1-induced vasoconstriction resulted in rapid and pronounced vasodilation (Group 6, FIG. 3).

No significant changes in arterial blood pressure or heart rate occurred with administration of either SNP or NTG.

These experiments establish that donors of NO (SNP and NTG) can rapidly and completely reverse cerebral vasoconstriction induced by ET-1. This effect is not associated with any change in systemic blood pressure or other vital signs under the conditions outlined.

The use of NO donor compounds to combat vasospasm in vivo has been limited (Afshar et al., 1995, J. Neurosurgery 83:118–122; Egemen et al., 1993, Neurology Research 15:310–315) and the threat of systemic hypotension following their administration has been an effective deterrent to their use in a clinical setting. The purposes of the experiments described herein was to demonstrate the effectiveness of NO donor compounds in reversing vasospasm when administered to the adventitial side of the cerebral blood vessel and to document this effect under direct visual observation without precipitating systemic hypotension.

The failure of SNP and NTG to induce hypotension when administered by this route is presumably related to the very short half-life (measured in seconds in the presence of oxygen) of NO in vivo (Culotta et al., 1992, Science 258:1862–1865). Its capacity for rapid diffusion, however, in part due to its small size, allows sufficiently effective penetration of the vascular wall to result in potent vasodilation.

These results, taken in the context of many other investigations specifically targeting ET-1 or NO in CDCV, are consistent with the hypothesis that CDCV simultaneously involves increased activity of endothelin-1 and decreased activity of its locally-acting physiologic antagonist, NO. This circumstance would theoretically be made possible by the simultaneous impact of oxyhemoglobin on the local concentration of ET-1 through gene activation and that of NO through direct binding to its heme moiety.

The experiments which were performed were conducted to answer the question of whether ET-1-induced vasoconstriction is susceptible to reversal by NO donor compounds administered adventitially. The results establish that it is.

Intrathecal administration of such nitric oxide donors thus represents an important therapeutic intervention for the treatment of chronic delayed cerebral vasoconstriction following SAH.

Example 2

ITSNP-Mediated Alleviation of Severe Cerebral Vasospasm in Three Human Patients

Chronic delayed cerebral vasoconstriction (CDCV) that follows aneurysmal subarachnoid hemorrhage (SAH) is the leading cause of mortality and neurological morbidity in human patients who initially survive rupture of a cerebral aneurysm. The most common treatment for CDCV following aneurysmal SAH is HHH therapy. Other interventions include intraarterial administration of papaverine or NO and balloon angioplasty. Severe cases of CDCV are sometimes refractory to HHH therapy, and some patients do not tolerate HHH therapy for medical reasons. For example complications of these interventions include congestive heart failure, disrythmias, and complications associated with Swan-Ganz catheterization, such as infection. For these reasons, an alternative treatment for CDCV is desirable.

The experiments described in Example 1 demonstrated the efficacy of nitric oxide-donating compounds in reversing severe cerebral vasoconstriction when administered adventitiously to blood vessels. The studies described in this Example demonstrate three instances in which medically refractory vasospasm was promptly and substantially reversed in human patients who had experienced aneurysmal subarachnoid hemorrhage (SAH). Vasospasm was alleviated in these cases by intrathecal administration of sodium nitroprusside (SNP), a nitric oxide (NO) donor. Alleviation of vasospasm in these patients was documented using clinical, angiographic, and ultrasonographic techniques. The studies described in this Example were performed as a part of a clinical study which was initiated following FDA approval.

Each of the three patients described in the studies of this Example experienced severe vasospasm, beginning from five to twelve days after sustaining aneurysmal SAH. All patients manifested stupor of new onset (Glasgow Coma Scale {GCS}=7; Teasdale et al., 1974, Lancet 2:81–84) and new focal neurological deficit (hemiplegia). Severe vasospasm was angiographically demonstrated in each of the three patients.

Each of the three patients was treated with intrathecally-administered sodium nitroprusside (ITSNP). Following ITSNP therapy, each of the three patients experienced reversal of vasospasm and relief from cerebral ischemia, which were documented by angiography, transcranial Doppler ultrasonography (TCD), and computed tomography (CT) as long as 54 hours after ITSNP therapy. Each patient also exhibited dramatic clinical improvement, two within several days, and the other within 12 hours. Complications related to intracranial pressure (ICP) elevation, changes in vital signs, and hemodynamic parameters were not detected during or following ITSNP therapy. Two of the three patients were discharged, and one remained hospitalized as of the time this description was prepared.

The studies described in this Example demonstrate that intrathecal administration of an NO donor compound alleviates severe vasospasm in human patients who have experienced SAH.

The materials and methods used in the studies described in this Example are now described.

Each of the three patients in the studies described in this Example exhibited symptomatic aneurysmal SAH-induced CDCV which was refractory to HHH therapy for one hour. TCD blood flow velocity measurements were used to diagnose CDCV in the context of clinical examination, and asymptomatic patients were not considered for inclusion in the studies described in this Example. For patients not available for clinical examination (e.g., patients under pentobarbital-induced EEG burst-suppression for brain protection), the decision regarding whether to include the patient in these studies relied more highly on TCD measurements than for patients who were available for clinical examination, although other study-inclusion criteria were considered (e.g., increase in intracranial pressure {ICP} or volume of CSF drainage when a physiological parameter {e.g., CSF drainage rate or ICP, respectively} was held constant). Patients having an obvious infarction or intra-parenchymal hematoma, as assessed by CT, patients with ICP that could not be reduced below 20 millimeters of mercury (gauge), and patients younger than 18 years of age were excluded from participation in this study.

For all patients, TCD velocity measurements were performed by a single operator specifically trained in the technique. TCD velocity measurements were normalized to account for varying hemodynamic conditions using the carotid index (mean blood flow velocity in the middle cerebral artery/mean blood flow velocity in the cervical internal carotid artery).

Cerebral angiography was performed using standard methods (transfemoral selective) before, during, and after ITSNP therapy, using a high-resolution bi-plane digital subtraction technique. In two of the patients (Patients #1 and #2 herein), additional post-treatment angiography was performed between 12 and 54 hours post-treatment. Cerebral circulation times, defined as the interval, in seconds, between the first observed filling of the ipsilateral carotid siphon and the first observed filling of either transverse sinus using an anteroposterior angiogram, were estimated to the nearest half-second and determined by a single observer for all patients. All cerebral circulation times were measured at constant mean arterial blood pressure (MABP). Blood vessel diameter was assessed digitally using the computer paradigm of the Phillips Integris 3000 Biplane Digital Subtraction Angiography Unit, by a single observer. These measurements were made using constant anatomical references which were discernable from the angiogram, such as bony landmarks or origins of readily observed branch vessels.

SNP was administered via ventriculostomy which was performed using standard methods involving cannulation of the lateral ventricle via the frontal lobe. The initial dosage range of SNP was based on experimental observations described herein in Example 1. The clinical response of patients to ITSNP therapy was assessed by intraprocedural monitoring and angiography.

Patients and Results

The characteristics of the patients involved in the studies of this Example, and the outcomes of ITSNP therapy of these patients are now described.

Patient #1 was a 42-year old woman who had sustained a Grade III SAH resulting from rupture of her left internal carotid artery bifurcation aneurysm, using the nomenclature of Hunt and Hess (Hunt et al., 1968, J. Neurosurg. 28:14–20). Patient #1 underwent uncomplicated craniotomy and clip ligation of the aneurysm within 24 hours following SAH. On the fifth day following SAH, the mental status Patient #1 had deteriorated, and this patient exhibited right-side weakness (GCS=7) which progressed to hemiplegia. The condition of Patient #1 failed to improve in response to either HHH therapy or cardiac performance enhancement with optimization of pulmonary capillary wedge pressure (PCWP), MABP, and cardiac index, as determined by Swan-Ganz catheterization. CT demonstrated low attenuation areas of left and right cerebral cortex, corresponding to the distributions of the right anterior cerebral artery, the left anterior cerebral artery, and the left middle cerebral artery. These observations are consistent with cerebral ischemia.

Cerebral angiography performed one hour following the onset of aggressive HHH therapy disclosed severe vasoconstriction of anterior circulation vessels bilaterally, including proximal and distal portions of the right anterior cerebral artery and the right posterior communicating artery, the proximal portion of the left anterior cerebral artery, the proximal portion of the left cerebral artery, and the distal portion of the left middle cerebral artery. Left-and right-side cerebral circulation times were 7 and 7.5 seconds respectively.

ITSNP therapy was performed on Patient #1 as follows. A total dose of 30 milligrams of SNP was delivered via ventriculostomy into the right lateral ventricle of Patient #1 in 5.0 milliliters aliquots of a 1.0 milligram per milliliter (in the admixed solution) solution of SNP which was dissolved in saline and then admixed with the patient's CSF prior to administration. Immediately prior to injection of this solution, a volume of CSF equal to or slightly greater than the injected volume was withdrawn from the ventriculostomy. ICP was monitored. Hemodynamic properties such as MABP were continuously monitored using a Swan-Ganz intracardiac catheter. Neurophysiologic properties were also monitored continuously by electroencephalography (EEG) and somatosensory evoked potential (SSEP) detection. Angiography was performed before, during, and after ITSNP therapy at fifteen minute intervals to visualize arteries distal to the left internal carotid artery.

Progressive and marked increase in the caliber of multiple previously constricted vessels was observed beginning with the angiogram obtained thirty minutes following the onset of ITSNP therapy. There was no significant change in MABP, ICP, or neurophysiologic parameters from baseline values during or after ITSNP therapy. TCD blood flow velocity measurements following ITSNP therapy were within normal limits, with the exception of the left middle cerebral artery. Blood flow velocity in this artery was initially normal following ITSNP therapy, and became moderately elevated (mean velocity <200 centimeters per second) twenty hours following ITSNP therapy. TCD measurements remained unchanged from this elevated value twenty-six hours following the procedure.

A cerebral angiogram performed twenty-four hours after treatment demonstrated persistent and substantial dilatation of the previously spastic right posterior communicating artery and the distal portion of the right anterior cerebral artery. This angiogram also demonstrated significant further increase in the dilatation of the M1 and M2 segments of the middle cerebral artery and the A1, A2, and A3 segments of the left anterior cerebral artery. Enhanced distal circulation was detected in both hemispheres. Relative diameters of cerebral vessels measured digitally before and after ITSNP therapy. These relative measurements are listed in Table 2. Left- and right-hemisphere cerebral circulation times were each reduced to 5 seconds.

TABLE 2

| | Artery Caliber | | % of baseline |
|---|---|---|---|
| | pre-treatment | 24 hours post-treatment | caliber |
| R A1 | 0.96 | 1.93 | 201 |
| R PcoA | 0.93 | 1.94 | 208 |
| L A1 | 0.93 | 2.00[A] | 215 |
| L M1 | 1.96 | 2.48 | 127 |
| L M2 | 0.93 | 2.16[A] | 232 |
| L A3 | 0.93[A] | 2.16 | 232 |

Note: [A]Estimated

CT analysis of the brain of Patient #1 was performed 48 hours after treatment, and indicated improvement in the oxygen supply to the previously ischemic areas.

Cerebral angiography was repeated fifty-four hours following ITSNP therapy, owing to the increased TCD velocity observed in the M1 segment of the left middle cerebral artery. The dilated appearance of the right-hemisphere blood vessels and the A1 and A2 segments of the left anterior cerebral artery persisted. Focal narrowing was observed in the M1 and proximal M2 segments of the left middle cerebral artery. The M1 segment of the left middle cerebral artery was angioplastied 54 hours following ITSNP therapy in order to restore to the segment the caliber produced by ITSNP therapy.

Patient #1 subsequently made a dramatic clinical recovery, emerging from coma and, within several days following ITSNP therapy, demonstrating useful function of her previously plegic right side. Useful function was more pronounced in the patient's right leg than in her right arm. Serum cyanate levels were determined to be undetectable on the evening following ITSNP therapy. Patient #1 was discharged in stable condition (GCS 15) to a rehabilitation facility within two weeks following ITSNP therapy. As of post-treatment day #129, Patient #1 was ambulatory with a walker at home, able to feed herself, and able to converse with a moderate pure motor dysphasia. Her right upper extremity remained densely paretic, although she was able to move it willfully.

Patient #2 was a 50 year-old man who had sustained a clinical Grade III (Hunt et al., 1968, J. Neurosurg. 28:14–20) and radiographic grade III (Fisher et al., 1980, Neurosurgery 6:1–9) SAH resulting from rupture of a right-side middle cerebral artery aneurysm. Patient #2's past medical history comprised a history of poorly-controlled arterial hypertension and a 50 pack per year history of cigarette smoking.

This patient underwent uncomplicated right pterional craniotomy and clip ligation of the aneurysm the day after the SAH occurred. Surgery was remarkable for an extremely swollen, injected-appearing brain with copious SAH despite effective osmotic diuresis and ventricular drainage. Temporary occlusion time of the inferior division of the right middle cerebral artery was 5 minutes under etomidate burst suppression anesthesia. No changes in neurophysiologic monitoring parameters (EEG and SSEP) were observed during the operation. The bone plate was not replaced at the end of the operation, in anticipation of cerebral swelling.

The patient awakened uneventfully and was extubated the day following surgery. He had no demonstrable focal neurologic deficit for five days and his GCS score was consistently 14–15. On the fifth day following surgery (i.e., the sixth day after the SAH occurred), the patient manifested an aggravated increase in TCD velocities on the left side, and simultaneously exhibited a profound depression in mental status (GCS 7) and an inability to move the right side of his body. He was emergently intubated.

CT scan of the brain demonstrated right-side cerebral swelling, moderate ventriculomegaly relative to his admission CT scan, and persistent residual SAH. No focal injury to the left cerebral hemisphere was discernible radiographically. A ventriculostomy was placed to enable ventricular decompression. ICP remained between 15 and 18 millimeters of mercury (gauge). No significant improvement in neurologic status was observed after one hour, despite optimization of HHH therapy.

Patient #2 was taken emergently for cerebral angiography, which demonstrated severe narrowing of the A1 segment of the right anterior cerebral artery, the A1 segment of the left anterior cerebral artery, and the M1 segment of the left middle cerebral artery. Cerebral circulation time was 8 seconds in the left hemisphere and 6.5 seconds in the right hemisphere. Increased SSEP latencies representing the right upper and lower extremities observed at baseline before intervention were believed to be consistent with the angiographic demonstration of vasospasm in the left middle cerebral artery and anterior cerebral artery distribution.

ITSNP was then performed on Patient #2 as follows. A total dose of 30 milligrams of SNP was delivered via ventriculostomy of Patient #2 in aliquots of a 4.0 milligram per milliliter solution of SNP which had previously been dissolved in saline before admixture with the patient's CSF. The first aliquot had a volume of 2.0 milliliters, and 20 minutes were permitted to elapse before administration of subsequent 1.0 milliliter aliquots at intervals of 5 to 10 minutes for a total of 53 minutes. The circumstances of administration in terms of neuroanesthetic and neurophysiologic monitoring were identical to those for Patient #1.

Improvement in the previously prolonged latencies of the left cortical SSEP was observed within 23 minutes of ITSNP therapy, the values decreasing from 23.9 milliseconds to 20.0 milliseconds for the upper extremity and from 51.5 milliseconds to 47.7 milliseconds for the lower extremity. At first, no significant change was observed in the caliber of the larger conductance vessels (segment A1 of the left anterior cerebral artery and the M1 segment of the left middle cerebral artery), and concurrent cerebral angioplasty was attempted. However, owing to the remarkable tortuosity of the patient's left internal carotid artery, the balloon catheter could not be navigated beyond the carotid siphon. ITSNP therapy continued, and progressive dilation of the M1 segment of the left middle cerebral artery became apparent. Although ITSNP therapy was stopped upon administration of a total dose of 30 milligrams of SNP, angiographic improvement continued. For this reason, no further attempt to perform angioplasty was made. Left-side cerebral circulation time improved from 8 seconds to 6 seconds. Circulation time on the right was also reduced to 5.5 seconds.

Fifty-five minutes following administration of the final SNP aliquot, the baseline diameter of the M1 segment of the left middle cerebral artery appeared to have been nearly restored, and the posterior communicating artery exhibited improved filling. Large-caliber vessels on the right showed minimal dilation, but the distal A1 segment of and the distal anterior cerebral artery in the interhemispheric fissure were better visualized following ITSNP therapy.

No important systemic hemodynamic changes were observed during or following ITSNP therapy. Hypotension did not occur. ICP elevation to 21 millimeters of mercury (gauge) occurred transiently after the first dose and responded promptly to 3 milliliters of ventricular drainage. ICP elevation did not occur subsequently, remaining at or below 17 millimeters of mercury (gauge). Neurophysiologic parameters remained stable during and following ITSNP therapy.

The patient was returned to the Neurosurgical Intensive Care Unit (NICU) where TCD velocity measurements were demonstrated to be dramatically improved. The same evening, the patient demonstrated consistent purposeful movement of his previously plegic right side. Subsequent elevation of TCD velocities on the contralateral (right) side led to repetition of cerebral angiography, and angioplasty was performed upon the right supraclinoid carotid artery approximately 12 hours following ITSNP therapy.

An angiogram was also performed on the left hemisphere and demonstrated recurrent narrowing of the A1 and M1 segments that had been previously dilated by ITSNP therapy. Cerebral circulation times were 5.5 and 6 seconds for right and left hemispheres, respectively. Endovascular maneuvers using a smaller balloon catheter and a hydrophilic guide wire permitted navigation of the patient's tortuous left internal carotid artery and the M1 segment was angioplastied concurrently with the administration of 12 milligrams of additional SNP in order to enhance distal circulation in resistance vessels. Neither the supraclinoid carotid nor the A1 segment was angioplastied. Cerebral circulation times decreased to 5 seconds bilaterally within 60 minutes of concurrent ITSNP therapy and angioplasty. Again, no hemodynamic or physiologic changes were observed during or following ITSNP therapy. MABP remained constant at 125 millimeters of mercury (gauge).

The following day the patient was awake and alert, and exhibited a GCS of 10. The patient followed commands briskly using all extremities. Serum cyanate levels were undetectable in samples drawn on the evening following treatment. CT imaging of the brain 5 days following treatment demonstrated improvement in cerebral swelling. This patient was millimeters of mercury (gauge) uneventfully discharged with no demonstrable neurological deficit (GCS= 15).

Patient #3 was a 38 year-old female who had sustained a clinical SAH grade 3 (Hunt et al., 1968, J. Neurosurg. 28:14–20) and radiographic SAH grade 3 (Fisher et al., 1980, Neurosurgery 6:1–9) aneurysmal SAH resulting from a ruptured right carotid ophthalmic segment aneurysm. This patient had no significant past medical history, but demonstrated clinical evidence of significant cardiac dysfunction of unclear etiology (cardiac left ventricular ejection fraction 35%).

Coil embolization of the aneurysm was recommended and performed in uncomplicated fashion on the second day of Patient #3's hospital stay, which was the fourth day after she had sustained the SAH. Full-scale heparinization was instituted during the course of coil embolization and was continued for 24 hours in routine fashion. Nimodipine, Decadron and Dilantin were administered to the patient in routine fashion. The patient remained in the NICU without complication.

TCD velocity measurements were made to determine Patient #3's carotid index. The carotid index increased on the second post-operative day (the sixth day post-SAH) to 8.5 on the right side and 9.2 on the left side. No other clinical changes were observed. Intravascular volume expansion was carried out in routine fashion using Swan-Ganz catheterization. On the eighth day post-SAH, carotid index values were again measured, and again increased, to 8.5 on the right side and 9.3 on the left side. The patient exhibited no neurological symptoms. Cardiac performance was optimized and pulmonary capillary wedge pressure was maintained at 14 millimeters of mercury (gauge).

Because of the patient's intrinsic cardiac dysfunction, the cardiac index did not surpass 3.25. On the ninth day post-SAH, carotid index values once again increased, to 9.6 on the right side and to 5.8 on the left side. Neosynephrine and dopamine were added to the regimen. MABP was maintained between 110–120 millimeters of mercury (gauge). On the tenth day post-SAH, Patient #3 experienced right-side hemiparesis and aphasia, and the patient's MABP fell to 80 millimeters of mercury (gauge), a decrease precipitated by bacteremia. The cerebral symptoms were resolved promptly upon restoration of the MABP above 90 millimeters of mercury (gauge). Antibiotic treatment was begun. On the eleventh day post-SAH, the patient was diagnosed with aspiration pneumonia. In the evening, the patient again experienced transient hemiparesis and aphasia in conjunction with a transient decrease in the MABP.

On the twelfth day post-SAH, carotid index values remained markedly elevated, but the patient demonstrated no neurological symptoms. The patient's body temperature increased to 39 degrees Celsius, and the antibiotic regimen was adjusted. Chest radiographs demonstrated pulmonary edema, and arterial oxygen saturation was marginal. Intubation was carried out electively. Patient #3 subsequently manifested right-side hemiplegia and aphasia. She was stuporous, and exhibited a GCS of 7. The patient's MABP was 110 millimeters of mercury (gauge), and her cardiac index was 4.0. A frontal ventriculostomy was placed and the patient was taken emergently for CT scan of the brain.

The CT scan was unremarkable, and the patient was taken to the angiography suite directly from CT. Cerebral angiography disclosed severe vasoconstriction of the M1 segment of the left middle cerebral artery, the M1 segment of the right middle cerebral artery, the left supraclinoid carotid artery, the right supraclinoid carotid artery, and the A1 segment of the right anterior cerebral artery. Cerebral circulation time in the left hemisphere was prolonged to 8 seconds and to 7.5 seconds in the right hemisphere. ICP was 10 millimeters of mercury (gauge). Balloon angioplasty of the M1 segment of the left middle cerebral artery and both supraclinoid carotid segments was performed. Angioplasty of the M1 segment of the right middle cerebral artery and the A1 segment of the right anterior cerebral artery could not be accomplished for technical reasons.

ITSNP therapy was performed on Patient #3 as follows. A total of 10 milligrams of SNP was delivered via the ventriculostomy in two aliquots of 1.25 milliliters of a 4 milligram per milliliter solution. Blood pressure and ICP remained stable during and following ITSNP therapy. Within 20 minutes following angioplasty and ITSNP therapy, left-side cerebral circulation time improved to 6 seconds. Right-side cerebral circulation time improved to 6.5 seconds following ITSNP therapy (i.e., in the absence of angioplasty in the A1 or M1 segments), without appreciable change in the caliber of the larger conductance vessels on that side. The patient was returned to the NICU and pentobarbital coma was instituted to maintain an electroencephalographic burst suppression pattern.

TCD values measured seven hours following ITSNP therapy indicated a dramatic reduction in blood flow velocities in the left middle cerebral artery, but no change in blood flow velocity in the right middle cerebral artery. Slight increases in velocities were noted in the right anterior cerebral artery and the left anterior cerebral artery. TCD measurements twenty-one hours following ITSNP therapy demonstrated a substantial reduction in blood flow velocities in vessels that had not been subjected to angioplasty (i.e., the right middle cerebral artery, the right anterior cerebral artery, and the left anterior cerebral artery) and a further reduction in blood flow velocity in the left middle cerebral artery. The low velocities persisted and the patient was resuscitated from the pentobarbital coma after 5 days.

The patient continued to improve and did not experience recurrence of vasospasm. Patient #3's mental acuity remained high, without a trace of neurological deficit (GCS= 15). Volume expansion was maintained. Pressors (i.e., blood pressure modulating compounds such as epinephrine which tend to increase MABP) were gradually and uneventfully withdrawn. Cerebral angiography was not repeated. The ventriculostomy was discontinued after a trial of clamping demonstrated no further ventriculomegaly. CT analysis of the brain 10 days following ITSNP therapy indicated no residual abnormality. The patient was discharged 32 days post-SAH to a rehabilitation facility for a brief time for reconditioning purposes, and did not exhibit neurological deficit. She has since returned home and her condition is excellent seven months following ITSNP therapy.

The observations made in the studies described in this Example demonstrate that intrathecal delivery of NO donor compound compounds alleviates severe refractory cerebral vasospasm following aneurysmal SAH in humans. Furthermore, the alleviation of vasospasm effected by ITSNP therapy persisted far beyond the expected half-life of SNP in a biological system.

Of the three patients described in this Example, all of whom presenting in grave condition with profound neurological deficit, two have no residual neurological deficit, and the other patient is greatly improved and living at home relatively early (129 days) following ischemia-related neurological deterioration. Treatment of the latter patient, furthermore, was uncharacteristically delayed, as she had been hemiplegic from vasospasm for at least twelve hours before being available for ITSNP therapy.

The observed pattern of reversal of vasoconstriction following administration of SNP and delayed segmental recurrence of vasoconstriction is consistent with a mechanism of action that depends upon the presence and availability of a finite substrate, wherein the mechanism can be at least temporarily overwhelmed. Although the duration of relief effected by ITSNP therapy has not been definitively established, the relief reported in the studies described in this Example following intraventricular administration endured sufficiently long to relieve vasospasm and other symptoms attributable to critical brain ischemia. Furthermore, even if the duration of relief afforded by ITSNP therapy were found to be shorter than a desirable value, ITSNP therapy can be repeated as necessary, thereby providing relief enduring for a period as long as considered desirable.

Substantial and sustained vasodilation of large-caliber cerebral conductance vessels in response to ITSNP therapy was demonstrated in the studies described in the Example. Although not explicitly investigated in these studies, it appears that improvement in collateral circulation, effected by dilation of cerebral blood vessels smaller than those which were examined herein by angiography can have an equally important effect upon shortening of cerebral circulation time. This conclusion is supported by the observations made herein that cerebral circulation time was sometimes shortened without effecting a dramatic change in the size of the large-caliber conductance vessels which were visualized in these studies.

This conclusion is further supported by the fact that NO is known to effect vasodilation through a cyclic GMP-mediated protein kinase activation mechanism (Nathan, 1994, Cell 78:915–918; Thomas, 1997, Neurosurg. Focus 3:Article 3). This mechanism presumably functions not only at the level of large-caliber blood vessels, but also at the level of the arteriole, which is also a muscularized vessel. Without wishing to be bound by any particular theory of operation, it is believed that the NO molecule provided by ITSNP penetrated the adventitial surface of a blood vessel, activates the soluble form of guanylate cyclase which, in turn, converts GTP to cyclic GMP. This latter second messenger activates protein kinase activity, which causes relaxation of vascular smooth muscle, thereby resulting in vasodilation. The relatively thinner walls of smaller vessels, such as arterioles, possibly renders them more readily susceptible to the effects of NO donor compounds administered adventitially, causing them to respond faster, and improving cerebral circulation time.

Such effects are consistent with the known physical properties of NO, which is a very small molecule, and is therefore capable of penetrating tissues directly. This is most evident in its interaction with blood vessels, which it can penetrate from the adventitial surface. However, NO should also be expected to penetrate brain tissue and blood clots. It is also possible that ITSNP penetrates the parenchyma by way of the ependyma of the ventricle. If this occurs, the physiological effects of NO should be, at least to a degree, independent of ventricular CSF circulation.

The beneficial effects of vasodilatation by NO donor compound administration appear to be obtainable without inducing intracranial hypertension or systemic hypotension. Thus, subarachnoid vasodilatation can be effected by administering NO donor compound compounds even more locally than described herein. Such delivery methods include delivery by subarachnoid catheter or delivery intraoperatively. Targeted local therapy of this type would be a theoretical advantage where CSF pathways are compromised by brain swelling, since these methods do not rely upon CSF circulation for delivery of the NO donor compound.

The need to deliver an NO donor compound in a timely manner in order to alleviate established CDCV is emphasis. It is an established practice to perform cerebral angiography and plan alternative therapy for patients who are experiencing CDCV when HHH therapy has been maximized and this therapy has proven ineffective for one hour. Preferably, ITSNP therapy is not delayed to assess the efficacy of HHH therapy, but is instead performed as soon as possible after CDCV has been diagnosed, and more preferably even before CDCV has been diagnosed, as described in the prophylactic methods herein. For instance, although the clinical outcome was relatively good for Patient #1 in the studies described in this Example, that outcome might have been even better had ITSNP therapy been administered to this patient earlier.

It is possible that ITSNP therapy can be used to prevent recurrence of established CDCV, for example by increasing the total dose of SNP administered to the patient, by extending the period over which the therapy is performed, or both. Although ITSNP therapy was used in conjunction with angioplasty in the studies described in this Example, it is understood that ITSNP therapy can be used either in conjunction with angioplasty or not. The observations made herein that ITSNP therapy resulted in vasodilation which was both temporally and spatially distinct from vasodilation resulting from angioplasty demonstrate that ITSNP therapy does not rely upon angioplasty for its efficacy.

In anticipation that the present disclosure may be published in a forum not limited to experienced practitioners, it is emphasized that experimental administration of NO donor compounds in the manner described herein is a serious undertaking that should not be performed in the absence of intense clinical, neurophysiologic, and neuroanesthetic monitoring, and preferably also not in the absence of direct angiographic control, as in these studies. Particular caution should also be exercised when performing ITSNP under circumstances of longstanding (i.e., more than 4 hours) brain ischemia. Demonstration of frank infarction or significant intraparenchymal hematoma is a relative contraindication to the use of NO donor compounds in the manner described herein, both because of the risk of hemorrhagic conversion of infarction by reperfusion, and because of potential excitotoxic effects attributable to NO.

Preferably, ITSNP is performed upon patients with vasospasm that proves refractory to HHH therapy, such as vasospasm that fails to respond clinically within 60 minutes. If angiographic or neurophysiologic improvement is not observed within 30 minutes from the onset of ITSNP therapy, patients are preferably submitted to angioplasty where it is feasible (proximal conductance vessels not distal to the M1 segments of the middle cerebral arteries and the A1 segments of the anterior cerebral arteries). In instances in which neurophysiologic improvement (e.g., shortened SSEP latencies) is observed, but in which the only discernible angiographic improvements appear to be in collateral circulation and improved circulation time (i.e., without a dramatic increase in the diameter of relatively large-caliber spastic conductance vessels), cerebral angioplasty and ITSNP therapy are preferably combined.

The studies described in this Example demonstrate that intrathecal administration of an NO donor compound alleviates cerebral vasospasm without precipitating intracranial hypertension or systemic hypotension. Although these studies demonstrate angiographic and ultrasonographic evidence of alleviation of vasospasm, an equally or more important effect of ITSNP therapy can be enhancement of cerebral blood flow at the level of the microcirculation, which was not directly detected in these studies.

Example 3

Intrathecal Administration of Sodium Nitroprusside for Alleviation and Prevention of Cerebral Vasospasm Following Aneurysmal Subarachnoid Hemorrhage in Humans Intrathecal sodium nitroprusside (ITSNP) therapy was performed as described herein in order to alleviate cerebral vasospasm in patients experiencing such vasospasm following aneurysmal SAH or in order to prevent cerebral vasospasm in patients who had experienced aneurysmal SAH but who had not experienced cerebral vasospasm.

ITSNP therapy was performed a total of 18 times in 16 patients, four of whom had not experienced cerebral vasospasm. Each of the 16 patients had a secured aneurysm and experienced SAH having clinical, radiographic, or both, grades >3. In 81% of the patients the initial clinical SAH grade was >3, using the nomenclature of Hunt and Hess (Hunt et al., 1968, J. Neurosurg. 28:14–20). In all patients, the radiographic SAH grade was at least 3 (Fisher et al., 1980, Neurosurgery 6:1–9). In 81% of the patients, severe vasospasm which was refractory to HHH therapy was diagnosed prior to ITSNP therapy. All of the patients with established refractory vasospasm were in grave neurological condition prior to ITSNP therapy.

ITSNP therapy was performed under simultaneous angiographic control with extensive hemodynamic and neurophysiologic monitoring. ITSNP was delivered by ventriculostomy using a subdural catheter or by direct intraoperative suffusion. Endpoints for vasospasm treatment were 1) durable angiographic reversal of vasospasm, 2) failure of effect within 30 minutes, 3) adverse effect. Endpoints for preventive treatment were 1) post-SAH day #10 without vasospasm, 2) adverse effect. In 67% of cases ITSNP was used alone (without angioplasty) for treatment or prevention of vasospasm.

Angiography performed during and immediately following ITSNP therapy demonstrated amelioration or reversal of vasospasm in 88.9% of the patients who were experiencing vasospasm prior to ITSNP therapy. The overall neurological outcome of patients who received ITSNP therapy was good or excellent in 87.5% of the patients. Four months following ITSNP therapy, 71% of the patients were still in good or excellent neurological condition.

None of the four patients who underwent prophylactic ITSNP therapy developed clinical vasospasm.

Of the 16 patients observed in the studies described in this Example, one patient demonstrated a brief elevation in TCD values during an interruption in ITSNP therapy that resolved upon continuation of therapy. Three patients experienced nausea, which could be abolished by pre-therapy administration of ondansetron.

The results of the studies described in this Example demonstrate that ITSNP therapy is a safe and effective treatment for refractory cerebral vasospasm. Furthermore, these results demonstrate that prophylactic ITSNP therapy is safe and effective to prevent cerebral vasospasm following aneurysmal SAH.

Example 4

An Apparatus for Intrathecal Delivery of an NO Donor Compound

An intrathecal drug delivery device can be used for intrathecal administration of an NO donor compound. A diagram of such a device is illustrated in FIGS. 6A–6E. The device is an instrument which is capable of withdrawing CSF from the patient in a finite volume and allows the withdrawn fluid to be mixed with a predetermined amount of a pharmacologic agent (i.e., an NO donor compound). The NO donor compound is then delivered into the intrathecal compartment of the patient for treatment of cerebral vasospasm.

The device is designed specifically to render the withdrawal of a certain volume of CSF necessary prior to delivery of the pharmacologic agent while simultaneously limiting the amount of the agent that can be administered at one time. The device therefore provides a margin of safety that is helpful under the circumstances of intrathecal drug delivery, such as brain ischemia, elevated intracranial pressure and systemic hypotension.

The device is locked by means of a locking port coupled to the flow outlet (18) onto the existing CSF drainage system (e.g., ventriculostomy). CSF is withdrawn in the usual manner into the interior (12) of the first hollow body (10), using an outer plunger (14) in the same manner as any syringe. The withdrawal of a certain volume of CSF (e.g., 5.0 ml) allows the passive movement of the fluid into the interior (22) of the second hollow body (20) by means of the passive intake port(s) (19), wherein it makes contact with, and is mixed with a predetermined amount of the pharmacologic agent (30). The agent which is mixed into solution with the CSF can then be delivered via the CSF drainage system through a unidirectional valve (28) by depressing the inner plunger shaft (24). The agent in solution can then be "chased" with a volume of CSF from the outer chamber (12) by depressing the outer plunger shaft (14). The device can have a stopping mechanism (29) which prevents withdrawal of the inner plunger shaft (24). The head of the outer plunger shaft (16) is snugly slidably disposed within the outer chamber (12),and the head of the inner plunger shaft(26) is snugly slidably disposed within the outer chamber (12)

Figure 6A:
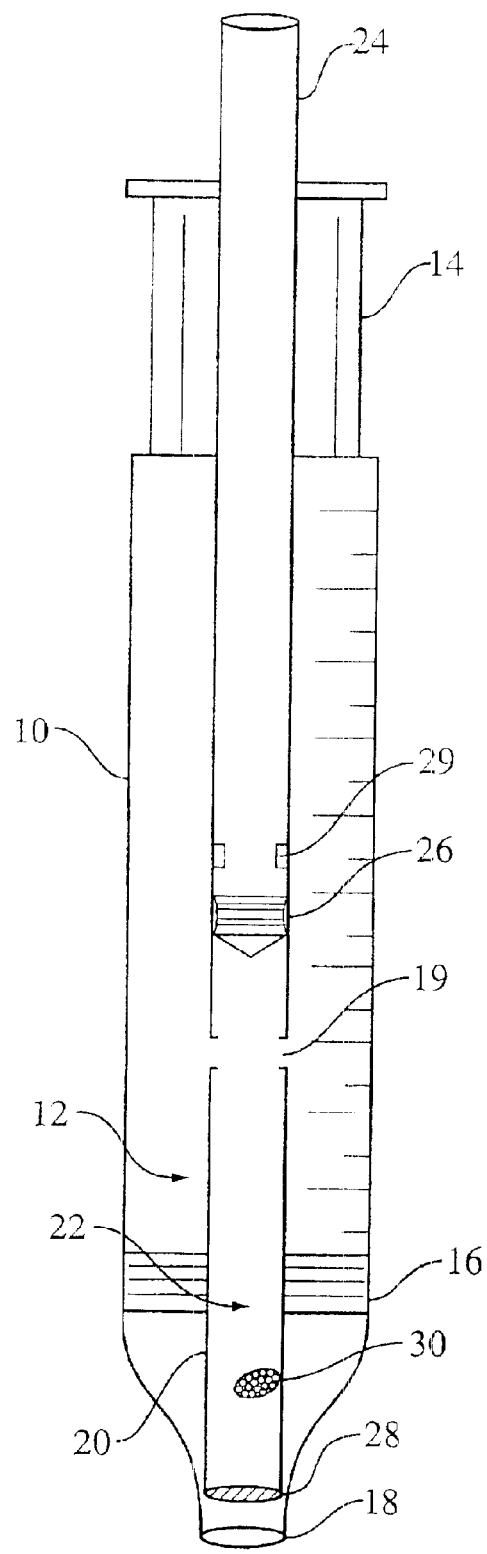
FIGS. 6A, 6B, 6C, 6D, and 6E, is a diagram of an apparatus for administration of NO intrathecally to a human.
Figure 6B:
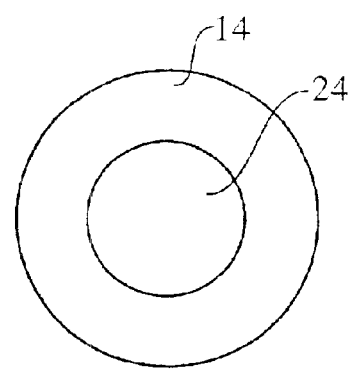
Figure 6C:
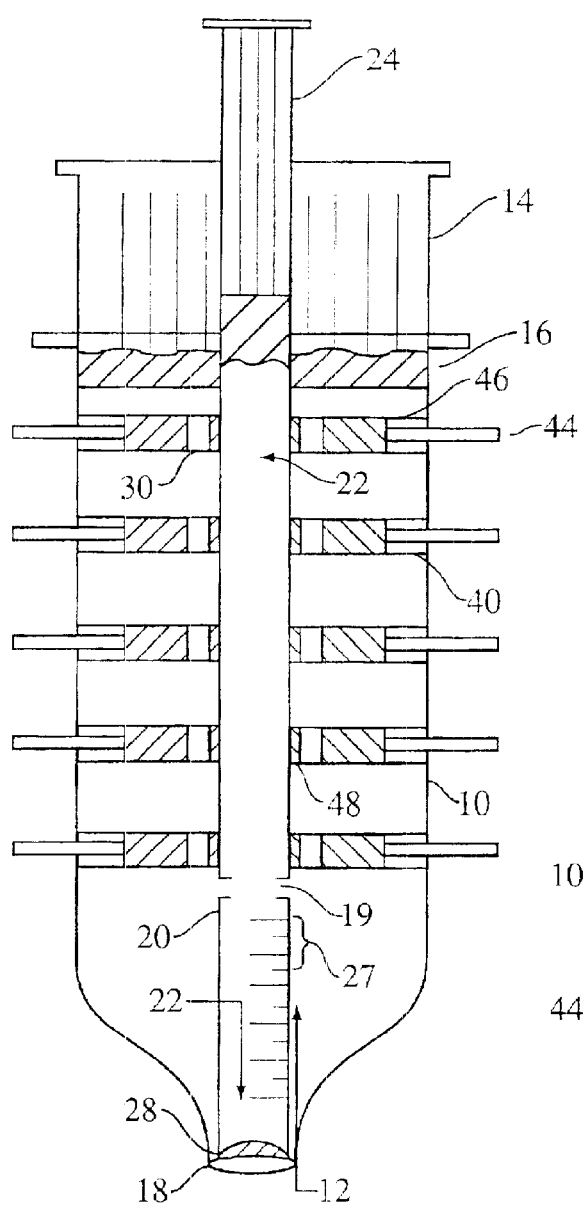
Figure 6D:
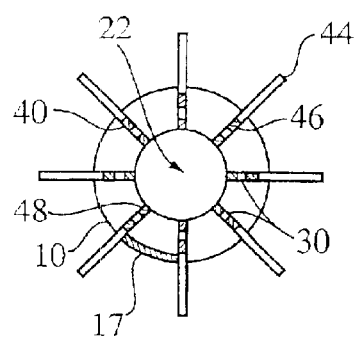
Figure 6E:
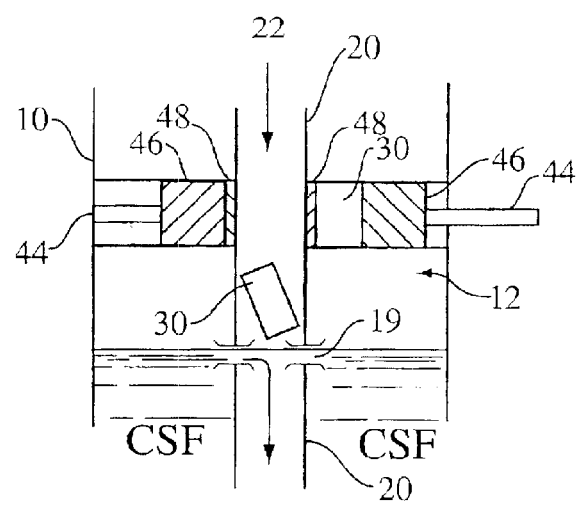

In an optional embodiment depicted in FIGS. 6C–6E, a plurality of predetermined amounts of the agent (30) are contained within compartments (40) which are separated from the interior (22) of the second hollow body (20) by a breachable barrier (48). The breachable barrier (48) of each compartment (40) can be breached by actuating a compartmental plunger (44) which urges the head of the compartmental plunger (46) against the agent (30), thereby breaching the barrier (48). The second hollow body (20) preferably has volumetric indicia (27) thereon to indicate the volume of fluid contained within the interior (22) thereof. The first hollow body (10) preferably has at least one transparent portion (17) through which the volumetric indicia (27) of the second hollow body (20) can be observed.

Example 5

A Subdural Catheter

The invention further includes a subdural catheter which can be used as a brain irrigation device. In one embodiment, the subdural catheter comprises a soft plastic catheter designed to evenly distribute fluid substances to the surface or to the interior (i.e., the ventricular system) of the brain. A diagram of this device is shown in FIGS. 7A through 7G. The catheter comprises has a body (50) made of inert plastic which is soft, flexible and radio-opaque (e.g., barium impregnated). Fluid or liquid medication is delivered to the device through the hub (54). The hub is designed to be locked onto a syringe or infusion tubing. The fluid or medication then travels through the lumen (56) of the catheter and subsequently can egress from the lumen through the perforations (52). The device has an extensive distribution of holes (52) which are present on the entire length of the catheter excluding the most proximal 3 cm. Further, the lumen is inversely tapered from proximal to distal, i.e., which gradually widens as the end of the catheter furthest from the hub is approached. Alternatively, or in addition, there can be a greater number of perforations (52) near the distal end than near the proximal end of the body (50), or the perforations (52) can be larger near the distal end than near the proximal end. This design permits even distribution of the fluid from the perforations along the entire perforated length of the catheter. Alternatively, the tip of the catheter can be sealed allowing egress only through the side perforations. As indicated in FIG. 7G, the catheter (C) can be used by attaching it to a fluid handling device, such as a syringe (S), and inserting the catheter (C) into a trephination (T) in the skull (Sk) of a patient.

Example 6

A Subdural Insertional Guide

Figure 8A:
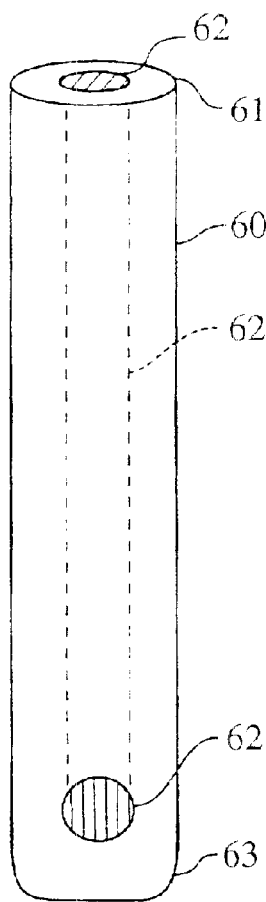
FIGS. 8A, 8B, 8C, and 8D, is a diagram of a subdural insertional guide.
Figure 8B:
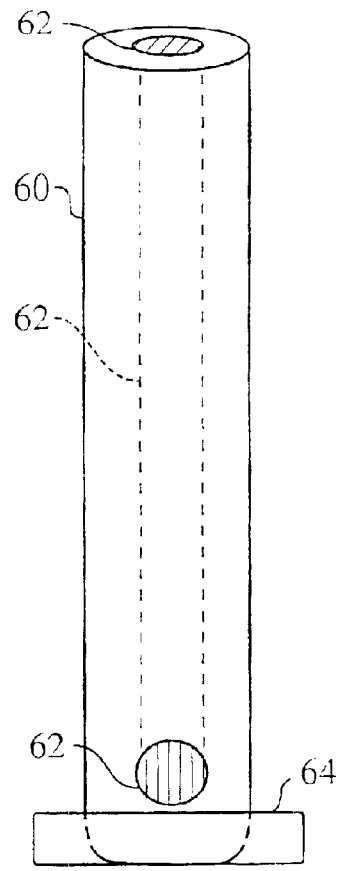
Figure 8C:
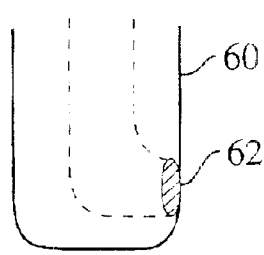
Figure 8D:
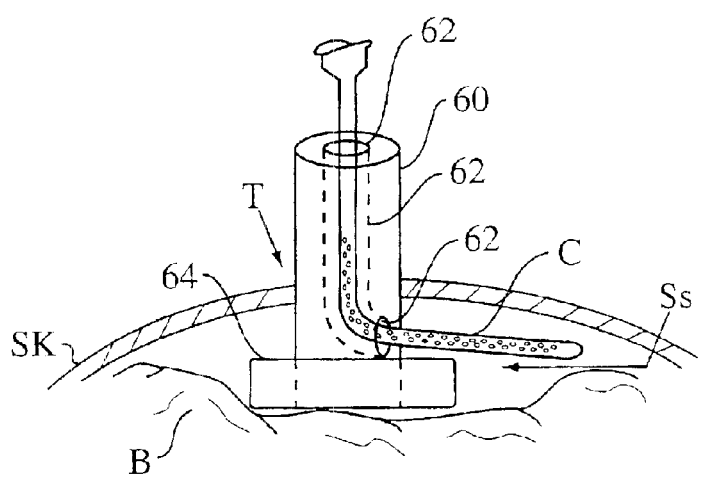

The invention also includes a subdural insertional guide which can be used, for example, as a subdural catheter implantation system. The subdural insertional guide comprises a rigid body (60) for delivery of a flexible catheter into the subdural space of the brain in a minimally invasive manner, as illustrated in FIG. 8. In one embodiment, the body (60) has a lumen (62) which makes a 90 degree turn within the device from vertical to horizontal with regard to the brain surface. This feature reduces the likelihood of brain penetration by the catheter and permits simple perpendicular trephination of the skull using a relatively small hole. The use of a small hole is preferable in both angled trephination (or drilling) and in making a larger bony opening. Once trephination is performed, the dura mater is surgically opened in the usual fashion and the device is inserted through the dural opening. The base of the device is relatively broad (e.g., about 15 millimeters) and can be used to gently depress the brain tissue at that site. Alternatively, the guide can be equipped with a circumferential balloon (64) at its base which can be inflated with air once inside the dura. The use of the balloon serves to effectively increase the diameter of the base to a safe width (approximately 15–20 millimeters) for depressing brain tissue and allows the cannula, and thus the trephination, to be narrower than it would be absent the use of the balloon. Upon gentle depression of the brain tissue (e.g., about 5–20 millimeters), the intradural catheter can be introduced through the proximal end (61) of the lumen (62) and passed through the body (60) to a portion of the lumen (62) which emerges at the external surface of the body (60) near the distal end (63) thereof. As indicated in FIG. 8D, the guide is used by inserting the body (60) into a trephination (T) in the skull (Sk) of a patient. The balloon (64), if present, is inflated, and brain tissue (B) beneath the trephination (T) is gently depressed. A catheter (C) is inserted into the lumen (62) at the proximal end (61) of the body (60), is urged through the lumen (62), and emerges in the subarachnoid space (Ss) in the patient.

Figure 9:
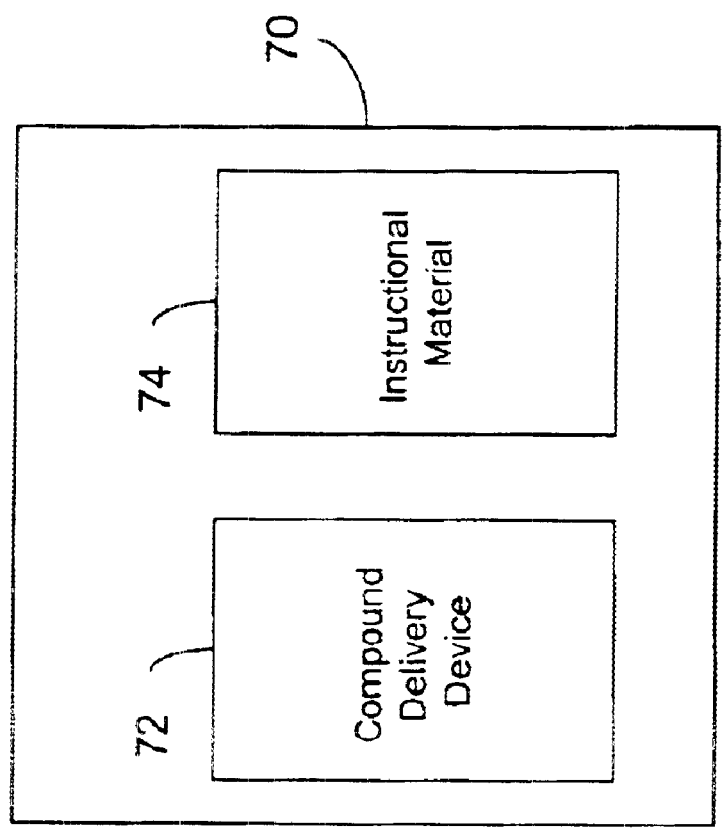
FIG. 9 illustrates a kit according to one embodiment.

With reference now to FIG. 9, a kit 70 for example for intrathecal administration of a nitric oxide donor compound includes a device 72 for example for administering the compound and instructional material 74 for example which describes use of the device to intrathecally administer the compound to a human.

The disclosures of each and every patent, patent application and publication cited herein are hereby incorporated herein by reference in their entirety.

While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A device for delivering a pharmacological agent in solution, the device comprising:
    a first hollow body having a flow orifice, a first fluid access port, and a first pressure orifice, each in fluid communication with the interior of the first hollow body;
    a second hollow body for containing the pharmacological agent, the second body having a second fluid access port in fluid communication with the interior of the second hollow body and in fluid communication with the first fluid access port, and an outlet port in fluid communication with the interior of the second hollow body;
    a first pressure modulator connected to the first pressure orifice; and
    a valve having an inlet orifice coupled to the outlet port and an outlet orifice, wherein the valve permits fluid flow in the direction from the inlet orifice to the outlet orifice.

2. The device of claim 1, wherein the outlet orifice is in fluid communication with the interior of the first hollow body.

3. The device of claim 1, wherein the second hollow body contains the pharmacological agent in the interior thereof.

4. The device of claim 3, wherein the pharmacological agent comprises a nitric oxide donor compound.

5. The device of claim 4, wherein the pharmacological agent comprises a single human intrathecal delivery amount of the nitric oxide donor compound.

6. The device of claim 1, further comprising at least one compartment containing the pharmacological agent, wherein the compartment is separated from the interior of the second hollow body by a breachable barrier.

7. The device of claim 6, wherein the breachable barrier is selected from the group consisting of a polymeric film and a foil.

8. The device of claim 7, wherein the film is selected from the group consisting of a film having at least one score and a film having at least one perforation.

9. The device of claim 6, further comprising a compartmental plunger slidably disposed within the compartment for breaching the barrier, wherein when the compartmental plunger is actuated, the barrier is breached, whereby the pharmacoloaical agent is brought into fluid communication with the interior of the second hollow body.

10. The device of claim 1, wherein the pressure modulator comprises a first plunger snugly slidably disposed within the interior of the first hollow body, the first plunger being positionable within the first hollow body between an advanced position and a retracted position, wherein the flow orifice is not in fluid communication with the fluid access port when the first plunger is positioned in the advanced position, and wherein the flow orifice is in fluid communication with the fluid access port when the first plunger is positioned in the retracted position.

11. The device of claim 10, further comprising a second plunger snugly slidably disposed within the second hollow body, whereby when the second plunger is urged in the direction of the outlet port, the contents of the second hollow body are discharged through the outlet port.

12. The device of claim 11, wherein the first hollow body is a first syringe, wherein the second hollow body is a second syringe, wherein the interiors of the first and second syringes are connected to the interior of a ventriculostomy by means of a multiple-way valve, wherein the multiple-way valve selectably connects any two of the interior of the first syringe, the interior of the second syringe, and the interior of the ventriculostomy.

13. The device of claim 1, wherein the second hollow body is disposed within the interior of the first hollow body; the first hollow body and second hollow body are substantially longitudinally coaxial; the outlet orifice is disposed in close proximity to the flow orifice; and the flow orifice is adaptable to a cerebrospinal fluid drainage system.

14. A kit for intrathecal administration of a nitric oxide donor compound to a human, the kit comprising:
    a) a device for administering the compound, the device comprising:
        a first hollow body having a flow orifice, a first fluid access port, and a first pressure orifice, each in fluid communication with the interior of the first hollow body;
        a second hollow body for containing the compound, the second hollow body having a second fluid access port in fluid communication with the interior of the second hollow body and in fluid communication with the first fluid access port, and an outlet port in fluid communication with the interior of the second hollow body; and a valve having an inlet orifice coupled to the outlet port and an outlet orifice, wherein the valve permits fluid to flow in the direction from the inlet orifice to the outlet orifice; and b) an instructional material which describes use of the device to intrathecally administer the compound to a human.

15. A kit for administration of a nitric oxide donor compound comprising:

a) a device for administering the compound, the device comprising:

a first body including a fluid access port, the first body defining a first volume;

a second body defining a second volume configurable to be in fluid communication with the first volume via the fluid access port; and a plunger disposed within the interior of the first body, the plunger being positionable within the first body between an advanced position and a retracted position, wherein the first volume and the second volume are not in fluid communication when the plunger is in the advanced position, and wherein the first volume and the second volume are in fluid communication when the plunger is in the retracted position; and b) an instructional material which describes use of the device to administer the compound.

16. A device capable of delivering a pharmacological agent in solution, the device comprising:

a first body defining a first volume, and a first fluid access port;

a second body defining a second volume configurable to be in fluid communication with the first volume via the fluid access port, said first and second volumes being substantially longitudinally co-axial and stationary with respect to each other during the use of the device; and a plunger slidably disposed within the interior of the first body, the plunger being positionable within the first body between an advanced position and a retracted position, wherein the first volume and the second volume are not in fluid communication when the plunger is in the advanced position, and wherein the first volume and the second volume are in fluid communication when the plunger is in the retracted position.

17. The delivery device as set forth in claim 16, further comprising a one-way valve operably affixed to the second hollow body, the valve selectively permitting fluid flow out of the second interior.

18. A delivery device configured for pharmacological agents comprising:

a first body including a fluid access port, the first body defining a first volume;

a second body defining a second volume configurable to be in fluid communication with the first volume via the fluid access port; and a plunger slidably disposed within the interior of the first body, the plunger being positionable within the first body between an advanced position and a retracted position, wherein the first volume and the second volume are not in fluid communication when the plunger is in the advanced position, and wherein the first volume and the second volume are in fluid communication when the plunger is in the retracted position.

19. The delivery device as set forth in claim 16, further comprising at least one compartment containing a pharmacological agent, wherein the compartment is in selective communication with the second volume.

20. A delivery device for mixing a user selected amount of pharmacological agent and fluid, and delivering a resulting solution, the delivery device comprising:

a first body including a fluid access port, the first body defining a first volume;

a second body defining a second volume configurable to be in fluid communication with the first volume via the fluid access port; and a plurality of compartments containing pharmacological agent doses, the plurality of compartments being separated from the second volume by a breachable barrier, where a user can urge the pharmacological agent doses from a selected number of compartments to provide a desired dosage.

* * * * *

UNITED STATES PATENT AND TRADEMARK OFFICE
CERTIFICATE OF CORRECTION

PATENT NO. : 6,796,966 B2
DATED : September 28, 2004
INVENTOR(S) : Jeffrey E. Thomas It is certified that error appears in the above-identified patent and that said Letters Patent is hereby corrected as shown below:

<u>Title page, Item [54] and Column 1, lines 1-3,</u>
Title, please change the title from "APPARATUS, AND KITS FOR PREVENTING OF ALLEVIATING VASOCONSTRICTION OR VASOSPASM IN A MAMMAL" to -- NITRIC OXIDE DONOR COMPOSITIONS, METHODS, APPARATUS, AND KITS FOR PREVENTING OR ALLEVIATING VASOCONSTRICTION OR VASOCPASM IN A MAMMAL --.

Signed and Sealed this

Twenty-ninth Day of March, 2005

JON W. DUDAS
*Director of the United States Patent and Trademark Office*

UNITED STATES PATENT AND TRADEMARK OFFICE
CERTIFICATE OF CORRECTION

PATENT NO.    : 6,796,966 B2
DATED         : September 28, 2004
INVENTOR(S)   : Jeffrey E. Thomas It is certified that error appears in the above-identified patent and that said Letters Patent is hereby corrected as shown below:

<u>Title page, Item [54] and Column 1, lines 1-3,</u>
Title, please change the title from "APPARATUS, AND KITS FOR PREVENTING OF ALLEVIATING VASOCONSTRICTION OR VASOSPASM IN A MAMMAL" to -- NITRIC OXIDE DONOR COMPOSITIONS, METHODS, APPARATUS, AND KITS FOR PREVENTING OR ALLEVIATING VASOCONSTRICTION OR VASOSPASM IN A MAMMAL --.

This certificate supersedes Certificate of Correction issued March 29, 2005.

Signed and Sealed this

Thirty-first Day of May, 2005

JON W. DUDAS
*Director of the United States Patent and Trademark Office*